(12) United States Patent
Rothberg et al.

(10) Patent No.: US 8,906,617 B2
(45) Date of Patent: Dec. 9, 2014

(54) METHODS FOR SEQUENCING INDIVIDUAL NUCLEIC ACIDS UNDER TENSION

(75) Inventors: Jonathan M. Rothberg, Guilford, CT (US); John H. Leamon, Guilford, CT (US); John F. Davidson, Guilford, CT (US); Antoine M. Van Oijen, Needham, MA (US); Wolfgang Hinz, Killingworth, CT (US); Melville Davey, Guilford, CT (US); Bradley Hann, Sierra Vista, AZ (US); Jonathan Schultz, Oxford, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/044,361

(22) Filed: Mar. 9, 2011

(65) Prior Publication Data

US 2011/0250700 A1 Oct. 13, 2011

Related U.S. Application Data

(63) Continuation of application No. 12/319,140, filed on Dec. 31, 2008.

(60) Provisional application No. 61/188,544, filed on Aug. 8, 2008, provisional application No. 61/191,930, filed on Sep. 12, 2008, provisional application No. 61/194,422, filed on Sep. 26, 2008, provisional application No. 61/197,588, filed on Oct. 29, 2008.

(51) Int. Cl.
  *C12Q 1/00* (2006.01)
  *C12Q 1/68* (2006.01)

(52) U.S. Cl.
  CPC ........ *C12Q 1/6874* (2013.01); *C12Q 2523/303* (2013.01)
  USPC ............... 435/6.11; 435/4; 435/6.1; 435/6.12

(58) Field of Classification Search
  None
  See application file for complete search history.

(56) References Cited

U.S. PATENT DOCUMENTS

| 4,597,002 | A | 6/1986 | Anthony |
| 6,168,948 | B1 | 1/2001 | Anderson et al. |
| 6,268,147 | B1 * | 7/2001 | Beattie et al. ................ 435/6.12 |
| 6,856,161 | B2 * | 2/2005 | Thewes ...................... 324/750.3 |
| 2003/0032052 | A1 | 2/2003 | Hadd et al. |
| 2003/0054396 | A1 | 3/2003 | Weiner |
| 2003/0068629 | A1 | 4/2003 | Rothberg et al. |
| 2003/0194740 | A1 | 10/2003 | Williams et al. |
| 2004/0142330 | A1 | 7/2004 | Nyren et al. |
| 2004/0207384 | A1 * | 10/2004 | Brederlow et al. .......... 324/71.5 |
| 2005/0009022 | A1 | 1/2005 | Weiner et al. |

(Continued)

FOREIGN PATENT DOCUMENTS

WO    WO 2005062049 A2 *  7/2005

OTHER PUBLICATIONS

Singh-Zocchi. Proceedings of the National Academy of Sciences. 2003. 100(13): 7605-7610.*

(Continued)

*Primary Examiner* — Robert T Crow
*Assistant Examiner* — Joseph G Dauner

(57) ABSTRACT

The invention provides apparatuses and methods of use thereof for sequencing nucleic acids subjected to a force, and thus considered under tension. The methods may employ but are not dependent upon incorporation of extrinsically detectably labeled nucleotides.

16 Claims, 23 Drawing Sheets

(56) References Cited

U.S. PATENT DOCUMENTS

| | | | |
|---|---|---|---|
| 2005/0029099 A1* | 2/2005 | Eversmann et al. | 204/416 |
| 2005/0062093 A1* | 3/2005 | Sawada et al. | 257/316 |
| 2005/0130173 A1 | 6/2005 | Leamon et al. | |
| 2006/0166203 A1 | 7/2006 | Tooke et al. | |
| 2006/0246443 A1* | 11/2006 | Bockelmann et al. | 435/6 |
| 2007/0172865 A1 | 7/2007 | Hardin et al. | |
| 2007/0184446 A1* | 8/2007 | Matsumoto et al. | 435/6 |
| 2008/0286878 A1* | 11/2008 | Vezenov | 436/94 |
| 2011/0015380 A1* | 1/2011 | Vezenov | 536/23.1 |

OTHER PUBLICATIONS

Antonarakis. Vogel and Motulsky's Human Genetics: Problems and Approaches. (2010) pp. 31-53.* den Dunnen. Hum Genet. (2001) 109: 121-124.*

Kim, S et al, "Multiplexed single molecule assay for enzymatic activity on flow-stretched DNA and Supplementary Note", *Nature Methods*, vol. 4(5), and *Supplementary Note*, pp. 397-399 (2007).

Maier, B et al, "Replication by a single DNA polymerase of a stretched single-stranded DNA", *PNAS*, vol. 97(22), pp. 12002-12007 (2000).

PCT/US09/04546 International Report on Patentability Mailed Feb. 17, 2011.

PCT/US09/04546 International Search Report Mailed May 17, 2010.

PCT/US09/04546 Written Opinion Mailed May 17, 2011.

Schurr, J M. et al, "Theory for the Extension of a Linear Polyelectrolyte Attached at One End in an Electric Field", *Biopolymers*, vol. 29, pp. 1161-1165 (1990).

* cited by examiner

SOURCE: APTINA

SOURCE: OMNIVISION

METHODS FOR SEQUENCING INDIVIDUAL NUCLEIC ACIDS UNDER TENSION

RELATED APPLICATIONS

This application is a continuation of U.S. application Ser. No. 12/319,140, filed Dec. 31, 2008, which claims priority under 35 U.S.C. §119(e) to U.S. Provisional Applications 61/188,544, 61/191,930, 61/194,422 and 61/197,588, filed Aug. 8, 2008, Sep. 12, 2008, Sep. 26, 2008 and Oct. 29, 2008, respectively, the entire contents of all of which are herein incorporated by reference.

BACKGROUND OF INVENTION

1. Field of Invention

The invention relates to methods and devices for sequencing nucleic acids, including DNA, under tension.

2. Discussion of Related Art

The elastic behavior of nucleic acids such as DNA has been investigated for a variety of purposes and using a variety of techniques. As an example, DNA has been stretched using electrical forces (Schurr et al. *Biopolymers* 29, 1161-1165 (1990)), electrophoresis (Smith et al. *Biopolymers* 1990, 1167-73 (1990)), hydrodynamic drag (Chu et al. *Science* 253, 861-866 (1991); Perkins et al. *Science* 268, 83-7 (1995); Yanagida et al. *Cold Spring Harb Symp Quant Biol* 47 Pt 1, 177-87 (1983); van Oijen et al. *Science* 301, 1235-8 (2003)), magnetic forces (Smith et al. *Science* 258, 1122-6 (1992)), glass needles (Cluzel et al. *Science* 271, 792-4 (1996)), optical traps (Smith et al. *Science* 271, 795-799 (1996); Bustamante et al. *Nat Rev Mol Cell Biol* 1, 130-6 (2000); Davenport et al. *Science* 287, 2497-500 (2000); Wuite et al. *Nature* 404, 103-6 (2000)), and optical tweezers (Wang et al. *Biophys. J* 72, 1335-1346 (1997)). Data from these studies have provided insights into DNA structure, and have revealed that when stretched by relatively low forces (e.g., less than or equal to 6 picoNewtons (pN)), single stranded DNA (ssDNA) is more compact than double stranded DNA (dsDNA). This difference in compactability is due in part to the shorter persistence length and increased incidence of secondary structure in ssDNA as compared to dsDNA (Kim et al. *Nat Meth* 4, 397-399 (2007)).

SUMMARY OF INVENTION

The invention relates broadly to methods, devices and systems for determining the sequence of individual nucleic acids. The methods require the synthesis of a nucleic acid strand that is complementary to the strand being sequenced and are thus referred to herein as sequencing-by-synthesis methods. More specifically, the methods determine sequence based on a change in the mechanical properties of the nucleic acid (as referred to herein, a template nucleic acid) upon incorporation of one or more nucleotides into the newly synthesized strand which is hybridized to the template nucleic acid, and consequently upon conversion of a single stranded region to a double stranded region of the template nucleic acid, particularly DNA.

In some of its broadest aspects, the invention provides methods for determining a nucleotide sequence of a nucleic acid that is under tension, and for synthesizing nucleic acids under tension. In some embodiments, a nucleic acid under tension is a nucleic acid that is subjected to a force that is at least about 1 pN up to and including about 12 pN. In some embodiments, the force is about 1 pN but less than 6 pN. In some embodiments, the force is greater than 6 pN and up to about 12 pN.

Thus, in one aspect, the invention provides a method for detecting incorporation of a nucleotide into a nucleic acid comprising contacting an immobilized nucleic acid with a nucleotide in the presence of a polymerase, detecting incorporation of the nucleotide into a newly synthesized nucleic acid hybridized to the immobilized nucleic acid based on a change in length of the immobilized nucleic acid while it is under tension. The newly synthesized strand may include a primer but it is not so limited.

In another aspect, the invention provides a method for determining incorporation of one or more nucleotides into a nucleic acid comprising contacting an immobilized nucleic acid with a plurality of identical nucleotides in the presence of a polymerase, determining whether incorporation of one or more of the plurality of identical nucleotides occurs in a newly synthesized nucleic acid hybridized to the immobilized nucleic acid based on a change in length of the immobilized nucleic acid while it is under tension. The newly synthesized strand may include a primer but it is not so limited.

In a related aspect, the invention provides a method for determining incorporation of one or more nucleotides into a nucleic acid comprising contacting an immobilized nucleic acid hybridized to a primer (including a hairpin primer) or other polymerase extendable substrate with a plurality of identical nucleotides in the presence of a polymerase, determining whether incorporation of one or more of the plurality of identical nucleotides occurs onto the primer based on a change in length of the immobilized nucleic acid while it is under tension.

In related aspects, the invention provides similar methods except that the plurality of nucleotides is not identical and may include two or three nucleotide types, provided the combination is known. For example, the plurality may be a mixture of dATP, dCTP and dGTP nucleotides, although it is not so limited. This plurality however is not a combination of all four known nucleotides. In these aspects, the immobilized nucleic acid is contacted with the mixture of nucleotides followed by contact with the remaining nucleotide(s) together or individually.

In some embodiments, the immobilized nucleic acid comprises a plurality of identical nucleic acid sequences conjugated to each other in tandem. In some embodiments, the plurality of identical nucleic acid sequences is at least 50, at least 100, at least 250, at least 500, at least 750, at least 1000, at least 10000, or at least 100000. In various embodiments, the plurality of identical nucleic acid sequences may be equal to or less than $10^8$, equal to or less than $10^7$, equal to or less then $10^6$, equal to or less than $10^5$, equal to or less than $10^4$, or equal to or less than $10^3$. Thus, the plurality of identical nucleic acid sequences may range from about 50 to about $10^8$, about 50 to about $10^7$, about 50 to about $10^6$, about 50 to about $10^5$, about 50 to about $10^4$, or about 50 to about $10^3$, without limitation.

In some embodiments, the immobilized nucleic acid is generated by rolling circle amplification (RCA). In some embodiments, the immobilized nucleic acid is generated by polymerase chain reaction (PCR).

In some embodiments, the immobilized nucleic is covalently immobilized to a solid support. In some embodiments, the immobilized nucleic is non-covalently immobilized to a solid support. Non-covalent immobilization may occur via biotin-avidin interactions, for example. In some embodiments, the immobilized nucleic acid is immobilized to a solid support via a linker. In some embodiments, the linker is polyethylene glycol (PEG). In some embodiments, the solid support comprises a plurality of different linkers, which may optionally be of differing lengths. In some embodiments, the plurality of different linkers comprise a plurality of polyethylene glycol of differing molecular weight (and length).

In some embodiments, the immobilized nucleic acid comprises a detectable moiety at its free end. In some embodiments, the detectable moiety is covalently attached to the free end of the immobilized nucleic acid. In some embodiments, the detectable moiety is a bead. In some embodiments, the bead is a magnetic bead.

A nucleic acid under tension refers to a nucleic acid experiencing a force, preferably along its length. In some embodiments, the immobilized nucleic acid is subjected to a flow-based force, a magnetic force, a mechanical force or an electrical force.

Various embodiments are recited below and it is to be understood that they apply to the various aspects recited herein.

In some embodiments, the immobilized nucleic acid is subjected to a force that is less than 6 picoNewtons (pN), between 5-6 pN, between 4-5 pN, between 3-4 pN, between 2-3 pN, or between 1-2 pN. In some embodiments, force is about 1 pN, about 2 pN, or about 3 pN. In some embodiments, the immobilized nucleic acid is subjected to a force that is greater than 6 pN and less than or equal to 12 pN.

In some embodiments, the immobilized nucleic acid is subjected to a magnetic force. In some embodiments, the immobilized nucleic acid is subjected to a magnetic force that is perpendicular to the flow-based force, or a magnetic force that is perpendicular to reagent flow. Thus, in some embodiments, the immobilized nucleic acid is subjected to more than one force (e.g., two forces).

In some embodiments, the polymerase is in solution. In some embodiments, the polymerase is tethered (attached) to the primer (or other polymerase extendable substrate) and/or the immobilized nucleic acid.

In another aspect, the invention provides a method for sequencing a nucleic acid comprising immobilizing a nucleic acid that comprises a plurality of tandemly arranged identical nucleic acids, performing a sequencing-by-synthesis reaction using the immobilized nucleic acid as a template, and detecting incorporation of nucleotides by changes in length of the nucleic acid.

In another aspect, the invention provides a method for sequencing a nucleic acid comprising immobilizing a nucleic acid that comprises a plurality of tandemly arranged identical nucleic acids onto a solid support surface, performing a sequencing-by-synthesis reaction using the immobilized nucleic acid as a template, and detecting incorporation of naturally occurring nucleotides. Naturally occurring nucleotides are minimally defined as nucleotides that lack extrinsic optical labels. This method may detect incorporation of nucleotides in the absence of fluorescence detection. The solid support surface may be a flat and continuous solid support surface.

Various aspects of the invention provide methods for detecting nucleotide incorporation in a non-enzymatic manner. This means that the methods do not require or rely on enzymes other than the polymerase used to incorporate the nucleotide(s). As an example, the invention does not require or rely on conversion of sequencing reaction byproducts (such as inorganic pyrophosphate) in order to detect nucleotide incorporation.

In another aspect, the invention provides a method for sequencing a nucleic acid comprising immobilizing a template nucleic acid on a solid support surface, wherein the template nucleic acid is hybridized to a plurality of primers and is bound to a plurality of polymerases, incorporating one or more known nucleotide triphosphates simultaneously at the 3' end of each primer, and detecting the incorporation of the one or more known nucleotide triphosphates by a change in length of the template nucleic acid.

In another aspect, the invention provides a method for sequencing a nucleic acid comprising immobilizing a nucleic acid that comprises a plurality of tandemly arranged identical nucleic acids onto a support surface, performing a sequencing-by-synthesis reaction using the immobilized nucleic acid as a template, and detecting incorporation of nucleotides non-enzymatically (e.g., in the absence of fluorescence detection).

In one embodiment, the nucleotides are naturally occurring nucleotides. In another embodiment, the nucleotides lack extrinsic detectable labels.

In some embodiments, the support surface is continuous. In some embodiments, the support surface is a non-continuous. In some embodiments, the support surface is a plurality of beads or particles such as but not limited to microparticles. The beads or particles may be solid or porous. In some embodiments, the support surface is rigid. In some embodiments, the support surface is porous such as a mesh.

In another aspect, the invention provides a method for sequencing a nucleic acid comprising immobilizing a nucleic acid that comprises a plurality of tandemly arranged identical nucleic acids onto a solid support, flowing oligonucleotides of known sequence over the immobilized nucleic acid, and detecting hybridization of the oligonucleotides to the immobilized nucleic acid by changes in length of the immobilized nucleic acid.

In some embodiments, different populations of oligonucleotides are flowed over the immobilized nucleic acid sequentially, and changes in length of the immobilized nucleic acid are measured between populations. The oligonucleotides may be 2, 3, 4, 5, 6, 7, 8, 9, 10, 15, 20, 25, 30, 35, 40, 45, 50 or more nucleotides in length.

In another aspect, the invention provides a method for sequencing a nucleic acid comprising immobilizing a plurality of nucleic acids that each comprises a plurality of tandemly arranged identical nucleic acids onto a solid support surface, performing a plurality of sequencing-by-synthesis reactions using the immobilized nucleic acids as templates, and detecting incorporation of nucleotides in the absence of fluorescence (i.e., in a non-fluorescent manner), wherein each of the plurality of template nucleic acids is bound to a separate region of the solid support surface that is contiguous and in fluid communication with all other regions on the solid support surface.

In another aspect, the invention provides a method for sequencing a nucleic acid comprising immobilizing a plurality of nucleic acids that each comprises a plurality of tandemly arranged identical nucleic acids onto a solid support surface, performing a plurality of sequencing-by-synthesis reactions using the immobilized nucleic acids as templates, and detecting incorporation of nucleotides for each individual immobilized nucleic acid. In some embodiments, each of the plurality of immobilized nucleic acids is bound to a separate region of the solid support surface that is contiguous and in fluid communication with all other regions on the solid support surface.

In another aspect, the invention provides a method for sequencing a nucleic acid comprising (a) immobilizing each of a plurality of template nucleic acids in separate non-overlapping regions of a solid support surface in a flow cell, each of the template nucleic acids comprising a plurality of tandemly arranged identical nucleic acid sequences and hybridized to a plurality of primers and bound to a plurality of polymerases, (b) introducing a plurality of known identical unlabeled nucleotide triphosphates into the flow cell, (c) for each individual template nucleic acid, detecting incorporation of one or more nucleotide triphosphates to the plurality of hybridized primers, (d) washing unincorporated nucleotide triphosphates from the flow cell, and (e) repeating steps (b) through (d) in the same flow cell using a different plurality of known nucleotide triphosphates, wherein all template nucleic acids within the flow cell are in fluid communication with each other.

In another aspect, the invention provides a method for sequencing a nucleic acid comprising performing a plurality of sequencing-by-synthesis reactions using a plurality of immobilized template nucleic acids each comprising a plurality of tandemly arranged identical nucleic acid sequences, wherein nucleotide incorporation is detected in a non-fluorescent manner. Sequences ranging in length from about 100-1000, about 200-1000, about 300-1000, about 400-1000, about 500-1000, about 600-1000, about 700-1000, about 800-1000 or about 900-1000 nucleotides (or bases) are determined from individual template nucleic acids. In other embodiments, about 200-900, about 300-800, about 400-700, or about 500-600 bases are determined from individual template nucleic acids. In still other embodiments, sequences in excess of 1000 bases are determined.

In another aspect, the invention provides a method for sequencing a nucleic acid comprising detecting incorporation of one or more known unlabeled nucleotide triphosphates to a plurality of primers hybridized to a template nucleic acid immobilized on a wall of a flow cell. In some embodiments, the flow cell is in contact with an optical detector or imager. In some embodiments, the wall is a CMOS contact imager. In some embodiments, the wall is a bottom wall.

In another aspect, the invention provides a method for sequencing a nucleic acid comprising fragmenting a nucleic acid to generate a target nucleic acid, individually amplifying a target nucleic acid to generate a template nucleic acid comprising tandemly arranged multiple copies of the target nucleic acid, and sequencing an individual template nucleic acid using unlabeled nucleotide triphosphates in the absence of fluorescence. The individual template nucleic acid may be sequenced based on change in length, as described herein.

In another aspect, the invention provides a method for sequencing a nucleic acid comprising individually sequencing a template nucleic acid that is immobilized on a solid support surface and is in fluid communication with other immobilized template nucleic acids using unlabeled nucleotide triphosphates.

In another aspect, the invention provides a method for generating a nucleic acid comprising isothermally amplifying a circular target nucleic acid using natural nucleotide triphosphates for a first set of amplification reactions and modified nucleotide triphosphates for a second set of amplification reactions to generate a template nucleic acid, wherein the first set of amplification reactions occurs prior to the second set of reactions.

In some embodiments, the second set of amplification reactions is a single ultimate (i.e., last or final) amplification reaction. In some embodiments, the second set of amplification reactions is a penultimate (i.e., next to last or next to final) and an ultimate amplification reaction.

In some embodiments, the modified nucleotide triphosphates comprises covalent or non-covalent reaction groups.

In some embodiments, the method further comprises attaching a detectable moiety to the template nucleic acid via the incorporated modified nucleotide triphosphates.

In some embodiments, the method further comprises attaching the template nucleic acid to a solid support.

In another aspect, the invention provides an apparatus comprising at least two polyethylene glycol populations immobilized to a solid support surface.

In some embodiments, the solid support surface is a glass surface. In some embodiments, the solid support surface is a CMOS imager.

In some embodiments, the at least two polyethylene glycol populations differ from each based on molecular weight (and typically length). In some embodiments, members of one or multiple polyethylene glycol populations are each attached to a biological agent.

In some embodiments, members of one polyethylene glycol population are attached to apyrase. In some embodiments, members of one polyethylene glycol population are attached to an oligonucleotide. In some embodiments, members of the polyethylene glycol population attached to an oligonucleotide are non-randomly immobilized on the solid support surface. In some embodiments, members of the polyethylene glycol population attached to apyrase are randomly immobilized on the solid support surface.

In some embodiments, the solid support surface is a bottom wall of a flow cell.

In another aspect, the invention provides an apparatus comprising a flow cell having an inlet and an outlet, and a wall having immobilized thereon in separate non-overlapping regions each of a plurality of nucleic acids, wherein the non-overlapping regions are in fluid communication with each other, and a CMOS imager.

In some embodiments, the nucleic acids are oligonucleotides ranging in length from 10-100 nucleotides. In some embodiments, the nucleic acids range in length from 100-$10^6$ nucleotides. In some embodiments, the plurality of nucleic acids is randomly distributed on the wall.

In some embodiments, the nucleic acids are conjugated to a detectable moiety at their free ends. In some embodiments, the detectable moiety is a bead. In some embodiments, the bead is a magnetic bead.

In some embodiments, the wall is a bottom wall. In some embodiments, the wall is comprised of glass.

In another aspect, the invention provides a method for measuring length comprising detecting a bead tethered to a known location on a solid support, and determining a distance moved by the bead over time.

In some embodiments, the bead is tethered to the solid support with a nucleic acid.

In some embodiments, the bead is detected using a contact imager. In some embodiments, the contact imager is a CMOS contact imager. In some embodiments, the solid support is a CMOS contact imager. In some embodiments, the bead is detected using an ISFET array.

In another aspect, the invention provides a method for determining a position of an observable moiety comprising detecting signal from an observable moiety, and subtracting from said signal a local average background signal, wherein the observable moiety is one of a plurality of observable moieties tethered to a solid support.

In some embodiments, the solid support is a contact imager. In some embodiments, the observable moiety is detected using an ISFET array.

In some embodiments, the local average background signal is calculated using signals from less than all pixels of the solid support. In some embodiments, local average background signal is calculated using signals from less than 5% of pixels of the solid support.

In some embodiments, the observable moiety is a bead. In some embodiments, the observable moiety is tethered to the solid support with a nucleic acid.

In another aspect, the invention provides a method for determining movement of an observable moiety that is tethered to a solid support comprising detecting a reference observable moiety and a test observable moiety, determining a level of movement of the reference observable moiety during a first time period to obtain a reference movement, and subtracting reference movement from a level of movement of the test observable moiety during the first time period, wherein the reference and test observable moieties are tethered to a solid support.

In some embodiments, the solid support is a contact imager. In some embodiments, the reference and test observable moieties are detecting using an ISFET array.

In some embodiments, the observable moiety is a bead. In some embodiments, the observable moiety is tethered to the solid support with a nucleic acid.

The foregoing aspects and embodiments of the invention will be discussed in greater detail herein. It should be understood that the invention contemplates any and all combinations of the foregoing aspects and embodiments, unless explicitly excluded herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 9A illustrates non-covalent attachment of DNA to a slide and non-covalent attachment of a bead to DNA. FIG. 9B illustrates covalent attachment of DNA to a slide and non-covalent attachment of a bead to DNA. FIG. 9C illustrates covalent attachment of DNA to a slide and covalent attachment of a bead to DNA.

DETAILED DESCRIPTION

The invention broadly provides high-speed, high-throughput methods, devices and systems for sequencing (i.e., determining the nucleotide sequence) of single nucleic acids. These methods, devices and systems can generate sequences on the order of tens or hundreds or thousands of bases per nucleic acid in a single read, and can do so simply, rapidly and in a cost-effective manner.

Figure 1:
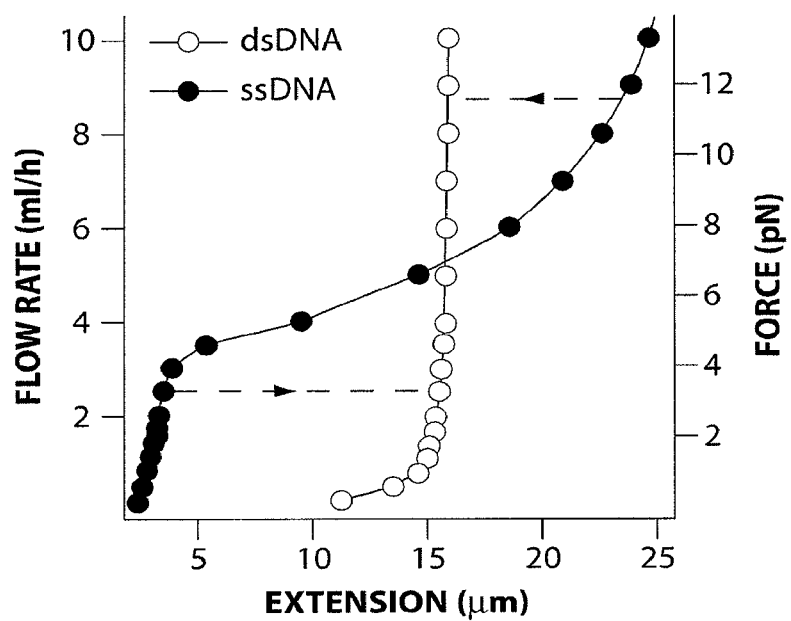
FIG. 1 is a graph showing the relationship between flow rate (left axis), force (right axis), and extension (bottom axis) using lambda phage single stranded (closed circles) and double stranded (open circles) DNA as a representative nucleic acid. Arrows illustrate DNA extension or shortening as a function of single or double stranded structure at low and high force. The Figure is taken from Kim et al. *Nat Meth* 4, 397-399 (2007).

It has been discovered according to the invention that the difference in the degree to which single stranded (ss) DNA and double stranded (ds) DNA can extend under identical force can be exploited to monitor nucleotide(s) incorporation into a growing strand of DNA, as occurs in a sequencing-by-synthesis process. Nucleotide incorporation is revealed by a change in the length of a template that is being sequenced. Whether the change in length is an increase or a decrease in length depends on the magnitude of force being applied to the template. As shown in FIG. 1, in the presence of forces up to and including 6 pN the template will increase its length with nucleotide incorporation, while in the presence of forces in excess of 6 pN the template will decrease its length with nucleotide incorporation. The magnitude of the change in length is proportional to the number of dNTPs incorporated and thus the method is not limited by the presence of a stretch of identical bases on a template. The forces used according to the invention can be but are not limited to flow-based force, magnetic force, mechanical force, and electrical force.

The methods of the invention therefore are not dependent on observing the incorporation (or cleavage) of detectable labels into the growing strand of DNA. In this regard, the methods described herein may be referred to as "label-free" methods, meaning that individual nucleotide triphosphates (dNTPs, or referred to herein simply as nucleotides) incorporated into the growing DNA strand need not comprise extrinsic labels in order to visualize their incorporation into the growing DNA strand. In other words, these dNTPs are "unlabeled".

Briefly, the methods provided herein contemplate the use of a nucleic acid template that is tethered on one end to a solid support (or substrate) and bound at its other end to a detectable (or observable) moiety such as but not limited to a bead. The template preferably comprises multiple copies of the nucleic acid molecule to be sequenced (i.e., the target nucleic acid), each copy with its own upstream primer binding site. Primers are bound to the template, polymerases are bound to the template/primer hybrid, and individual (or known combinations of) dNTPs are flowed over the template/primer hybrid. If the flowed dNTPs are complementary to the next unpaired nucleotide (or base) on the template (i.e., the single stranded base that is immediately adjacent to the 3' end of the newly synthesized strand or primed strand), then the dNTP will be incorporated into that strand. Similarly, if the next unpaired "n" nucleotides on the template are identical, then a plurality of the flowed dNTPs will be incorporated into the newly synthesized strand provided the requisite complementarity exists.

Incorporation of one or more dNTPs into the primed strand serves to convert a single stranded region of the template into a double stranded region, and this conversion manifests itself as a change in length when a force is applied to the template. Whether the change is an increase or a decrease in length depends on the magnitude of the force, as described herein.

The change in length may be determined by measuring the length of the tethered nucleic acid. Alternatively, it may be indicated by relative movement (or position) of the observable moiety on the free end of the tethered nucleic acid. By measuring (or determining) the position of the observable moiety after each nucleotide flow and/or wash, its relative position and movement can be determined and used to deduce whether nucleotides have been incorporated during the last nucleotide flowthrough.

Figure 2:
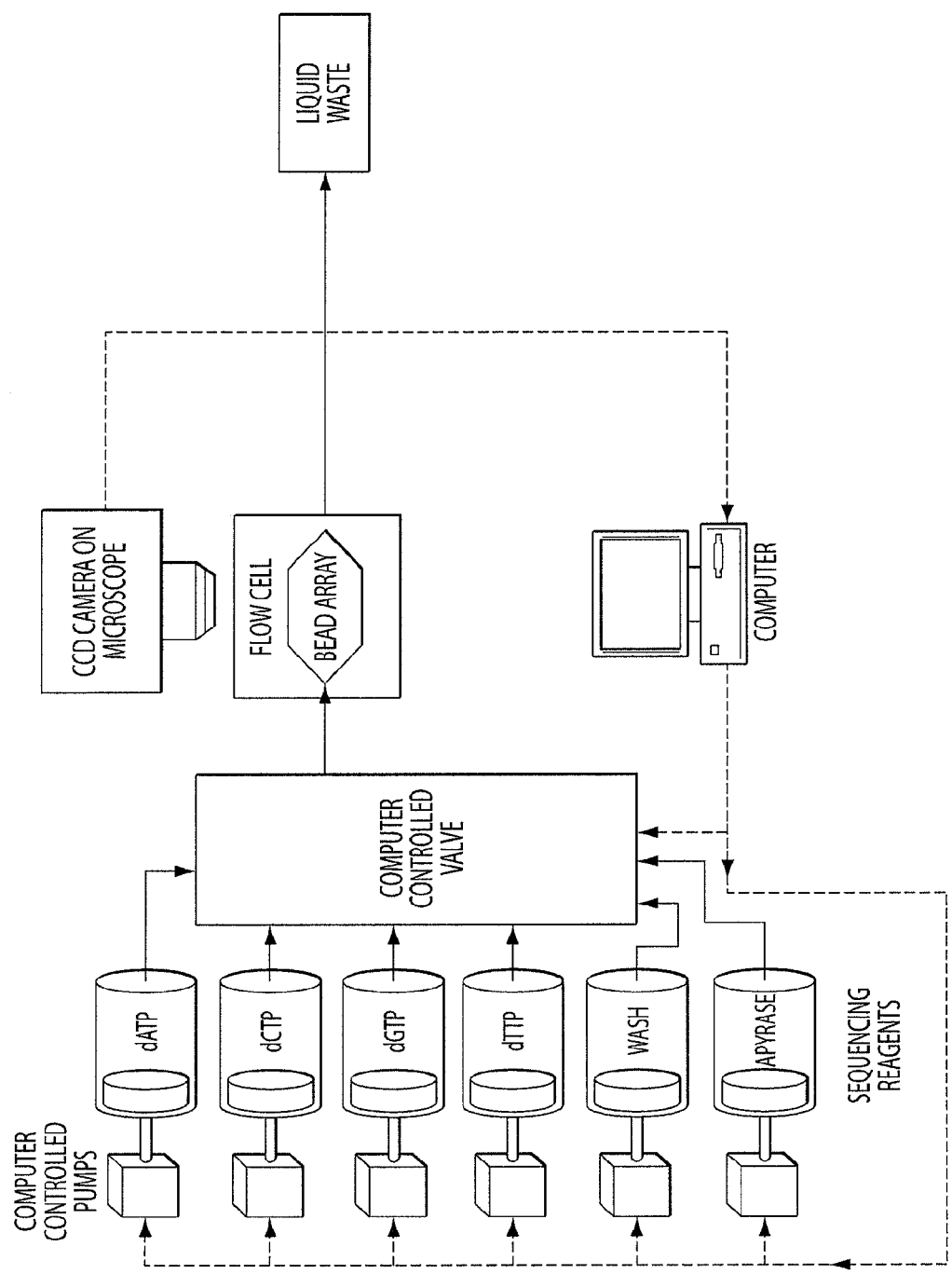
FIG. 2 is a schematic diagram of a system useful for sequencing nucleic acid molecules under tension, according to the invention.

Conversely, if the flowed nucleotides are not complementary to the next unpaired nucleotide in the template, then no nucleotides will be incorporated into the primed strand, no single-stranded to double-stranded conversion will occur, and there will be no discernable change in the length of the template. The process is repeated until all four nucleotides are flowed over the template/primer hybrids (i.e., a cycle), and then cycles are repeated until no further incorporation is detected. The nucleotide sequence of the template is determined by measuring whether and to what degree the template length changes as the nucleotides are cycled through. An exemplary schematic of the system that can be used to flow individual nucleotides over the immobilized nucleic acids is shown in FIG. 2.

Having described the method of the invention generally, each aspect of this method will be described in greater detail.

1. Targets, Templates and Solid Supports

As used herein, the nucleic acid being sequenced is referred to as the target nucleic acid (or the target). Target nucleic acids include but are not limited to DNA such as but not limited to genomic DNA, mitochondrial DNA, cDNA and the like, and RNA such as but not limited to mRNA, miRNA, and the like. The target nucleic acid may derive from any source including naturally occurring sources or synthetic sources. The nucleic acids may be PCR products, cosmids, plasmids, naturally occurring or synthetic library members or species, and the like. The invention is not intended to be limited in this regard. The nucleic acid may be from animal or pathogen sources including without limitation mammals such as humans, and microbes such as bacteria, viruses, fungi, parasites, and mycobacteria. In some embodiments, the nucleic acid is not a viral nucleic acid. The target nucleic acid can be obtained from any bodily fluid or tissue including but not limited to blood, saliva, cerebrospinal fluid ("CSF"), skin, hair, urine, stool, and mucus. The target nucleic acid may also be derived from without limitation an environmental sample (such as a water sample), a food sample, or a forensic sample.

Target nucleic acids are prepared using any manner known in the art. As an example, genomic DNA may be harvested from a sample according to techniques known in the art (see for example Sambrook et al. "Maniatis"). Following harvest, the DNA may be fragmented to yield nucleic acids of smaller length. The resulting fragments may be on the order of hundreds, thousands, or tens of thousands of nucleotides in length. In some embodiments, the fragments are 50-1000 nucleotides in length, 100-1000 nucleotides in length, 200-1000 base pairs in length, or 300-800 base pairs in length, although they are not so limited. Nucleic acids may be fragmented by any means including but not limited to mechanical, enzymatic or chemical means. Examples include shearing, sonication, nebulization and endonuclease (e.g., DNase I) digestion, or any other technique known in the art to produce nucleic acid fragments, preferably of a desired length. Fragmentation can be followed by size selection techniques used to enrich or isolate fragments of a particular length. Such techniques are also known in the art and include but are not limited to gel electrophoresis or SPRI.

Alternatively, target nucleic acids that are already of a desired length may be used. Such target nucleic acids include those derived from an exon enrichment process. See Albert et al. *Nat Meth* 4(11):903-905 (2007), Porreca et al. *Nat Meth* 4(11):931-936 (2007), and Okou et al. *Nat Meth* 4(11):907-909 (2007) for methods of isolating and/or enriching sequences such as exons prior to sequencing. Thus, rather than fragmenting (randomly or non-randomly) longer target nucleic acids, the targets may be nucleic acids that naturally exist or can be isolated in shorter, useable lengths such as mRNAs, cDNAs, exons, PCR products (as described above), and the like.

Generally, the target nucleic acids are ligated to sequences on one or both the 5' and 3' ends. These adaptor sequences comprise sequencing primer sites (i.e., sites to which a sequencing primer will hybridize) to be used in the sequencing methods of the invention. In some embodiments, these nucleic acids are then circularized and their circular forms are used to generate the template nucleic acids used in the sequencing methods, as discussed in greater detail below.

In some embodiments, the targets subjected to amplification, as discussed below, are of the same or similar length (e.g., a 5-10% variation between targets). In some embodiments, such variation may be kept as small as possible in order to ensure that all templates are uniformly applied.

In various embodiments, the invention exploits isothermal nucleic acid amplification to generate templates comprised of tandem repeats of the target nucleic acid (or more accurately, its complement). This typically can result in a plurality of linearized multi-kilobase nucleic acid strands, each comprising a plurality of tandemly repeated target nucleic acids (or complements thereof). The target nucleic acids within a given template are identical (or homogeneous), while the target nucleic acids between different templates are usually different (or heterogeneous). As used herein, a plurality of tandemly arranged identical nucleic acids means a plurality of identical nucleic acid sequences that are covalently attached in a linear manner. Illustrative examples are provided in FIGS. 9A-C and 11A-F.

Rolling circle amplification (RCA) (Fire et al. *Proc Natl Acad Sci* 92, 4641-4645 (1995); Liu et al. *J Am Chem Soc* 118, 1587-1594 (1996); Daubendiek et al. *J Am Chem Soc* 117, 7818-7819 (1995)) is an example of an isothermal nucleic acid amplification process that is capable of generating on the order of $10^4$ to $10^6$ fold linear amplification of a circularized nucleic acid (Lizardi et al. *Nat Genet.* 19, 225-32 (1998)). RCA has been employed for multiple purposes including signal amplification of DNA (Ladner et al. *Lab Invest* 81, 1079-1086 (2001); Nallur et al. *NAR* 29, e118 (2001)) and protein (Schweitzer et al. *Proc Natl Acad Sci USA* 97, 10113-10119 (2000)) arrays. Additionally, RCA reactions have been initiated from 5' amine-labeled primers covalently attached to the surface of a glass slide (Hatch et al. *Gen Anal* 15, 25-40 (1999); Lizardi et al. *Nat Biotechnol* 26, 649-50 (2008)). The amplified concatamers generated during the RCA process are single-stranded, accessible and have been amenable to hybridization to sequence-specific nucleic probes for amplification detection (Lizardi et al. *Nat Genet* 19, 225-32 (1998)) and sequencing-by-hybridization (Pihlak et al. *Nat Biotechnol* 26, 676-84 (2008)).

The RCA process involves circularization of a target nucleic acid that is covalently linked to an upstream primer site. Circularization can be accomplished either by the various traditional guide-based ligation processes (Fire et al. *Proc. Natl. Acad. Sci.* 92, 4641-4645 (1995); Lizardi et al. *Nat Genet* 19, 225-32 (1998); Diegelman et al. *Curr Protoc Nucleic Acid Chem* Chapter 5, Unit 5 2 (2001)) or by the direct application of single-stranded DNA ligase (Polidoros et al. *BioTechniques* 41, 35 (2006)). Either method of circularization is amenable to targets that are derived from synthetic oligonucleotides or from fragmented genomes as will be relevant to genomic sequencing (Pihlak et al. *Nat Biotechnol* 26, 676-84 (2008)). Following ligation (or circularization), recalcitrant, uncircularized nucleic acids and excess guides (if used), but not circularized nucleic acids, are degraded and thus effectively removed from the reaction mixture by the addition of 3' and/or 5' exonucleases.

The invention embraces the use of other approaches for generating concatamerized templates. One such approach is a PCR described by Stemmer et al. in U.S. Pat. No. 5,834,252, and the description of this approach is incorporated by reference herein.

Thus, as used herein, the template is the nucleic acid that contains one and preferably more than one copy of the target nucleic acid, each copy being linked to an upstream primer site. The template is tethered to a solid support (or substrate) prior to the sequencing-by-synthesis reaction of the invention. The template preferably contains at least 10, at least $10^2$, at least $10^3$, at least $10^4$, at least $10^5$, at least $10^6$, or at least $10^7$ concatamerized copies of the original nucleic acid to be sequenced. In various embodiments, the template may contain equal to or less than $10^8$, equal to or less than $10^7$, equal to or less then $10^6$, equal to or less than $10^5$, equal to or less than $10^4$, or equal to or less than $10^3$ concatamerized copies of the original nucleic acid to be sequenced. Thus, the number of concatamerized copies per nucleic acid may range from about 50 to about $10^8$, about 50 to about $10^7$, about 50 to about $10^6$, about 50 to about $10^5$, about 50 to about $10^4$, or about 50 to about $10^3$, without limitation. Each of the concatamerized copies within a template contains a common primer site to which sequencing primers can bind.

The amplified products can be immobilized to the support surface (e.g., a glass surface) in a variety of ways, some of which are discussed in greater detail here. In a first instance, the circularized target nucleic acid is hybridized to a primer that is itself immobilized on the support surface. The primer is then extended through the amplification process and in doing so this immobilized primer is part of the template nucleic acid. The amplification process in this example may be referred to herein as "solid-phase" since the amplification product is attached to a solid phase (i.e., the support surface) during the process.

In a second instance, the amplification process is carried out in solution and the final product is then attached to the support surface. The amplification product may be attached to the solid support at its 5' end or its 3' end. Attachment may be through hybridization to a nucleic acid that is immobilized to the support surface or it may be through interaction of moieties on the end of the amplification product with moieties on the support surface. Examples include the use of biotin or dual biotin labeled DNA (Margulies et al. *Nature* 437:376 (2005)) with streptavidin/avidin/neutravidin coated support surfaces, DIG (digoxigenin) and anti-DIG antibodies or antibody fragments, fluorescein and anti-fluorescein antibodies or antibody fragments (Gore et al. *Nature* 442, 836-9 (2006)), or through the use of heterofunctional cross-linkers such as biotinylated succinimidyl propionate-PEG which can be coupled for example to amine-functionalized glass and used to immobilize biotin-labeled DNA through a streptavidin sandwich (i.e., a nucleic acid biotin streptavidin/avidin/neutravidin-biotin solid support interaction).

The templates may be referred to as being randomly immobilized onto the surface. This means that the templates are not placed on the solid support surface based on sequence. They are however placed on the solid support in a manner that ensures that each template is surrounded by an area (and thus volume) that will not be occupied by another template during the polymerase-mediated incorporation reactions and/or during extension of the template. That is, in some instances, the templates are positioned on the surface at a sufficient distance from each other to prevent any interaction between the templates.

The solid support refers to the element to which the template is bound (or tethered or immobilized as the terms are used interchangeably herein with respect to templates on solid supports, and as discussed in greater detail below). The solid support can be comprised of any material, including but not limited to glass or other silica based material, plastic or other polymer based material, provided however that the material is relatively inert to template, primer, polymerase, dNTPs, apyrase, various linkers including those discussed herein, and other components used in the sequencing reaction and wash. The solid support may or may not be rigid. It may be porous. It may or may not be continuous. In some embodiments, the solid support is a glass slide. In some embodiments, the support is a plurality of beads or particles (such as microparticles) that are themselves immobilized onto a solid support. Such beads may be porous. The support may be a mesh. In some embodiments, the solid support is itself a detector or a sensor such as but not limited to a contact imager, an example of which is a CMOS contact imager.

It is to be understood that a plurality of templates whether identical or different may be tethered to the solid support, provided that each member of the plurality is sufficiently spaced apart from other members so that no overlap occurs between templates, particularly under tension. A discussion of the dimensions and density of packing of templates onto a solid support is provided elsewhere herein.

It is important that as many templates as possible remain on the solid support during the sequencing-by-synthesis reactions, particularly as they occur under tension. The magnitude of the force being applied to the templates will dictate to some extent the manner in which the templates should be immobilized. In some instances, the invention contemplates applying force to the templates gradually.

Some embodiments will employ a biotin-streptavidin interaction to tether templates. The force required to rupture a biotin-streptavidin bond (Taisuke et al. *Applied Physics Letters* 87, 043901 (2005)) is greater than the forces contemplated by the invention.

Other embodiments will employ covalent chemistries since the forces required to breaking a carbon-carbon bond are between 2.6 and 13.4 nN (Odell et al. *J of Pol Science Part B Pol Physics* 24, 1889-1916 (1986)), a force that is three orders of magnitude greater than the pN flow forces typically used to stretch DNA and contemplated by the invention. Covalently attaching the template to the solid support permits the use of significantly greater forces during the claimed method, if desired. Such forces may be used to remove primers and/or newly synthesized strands from the immobilized templates. Primers and DNA strands may be removed in the presence of low salt, high pH, and/or detergent. Such "stripping" of the template can allow for the repeated sequencing of the same templates in order to increase accuracy.

Figure 5:
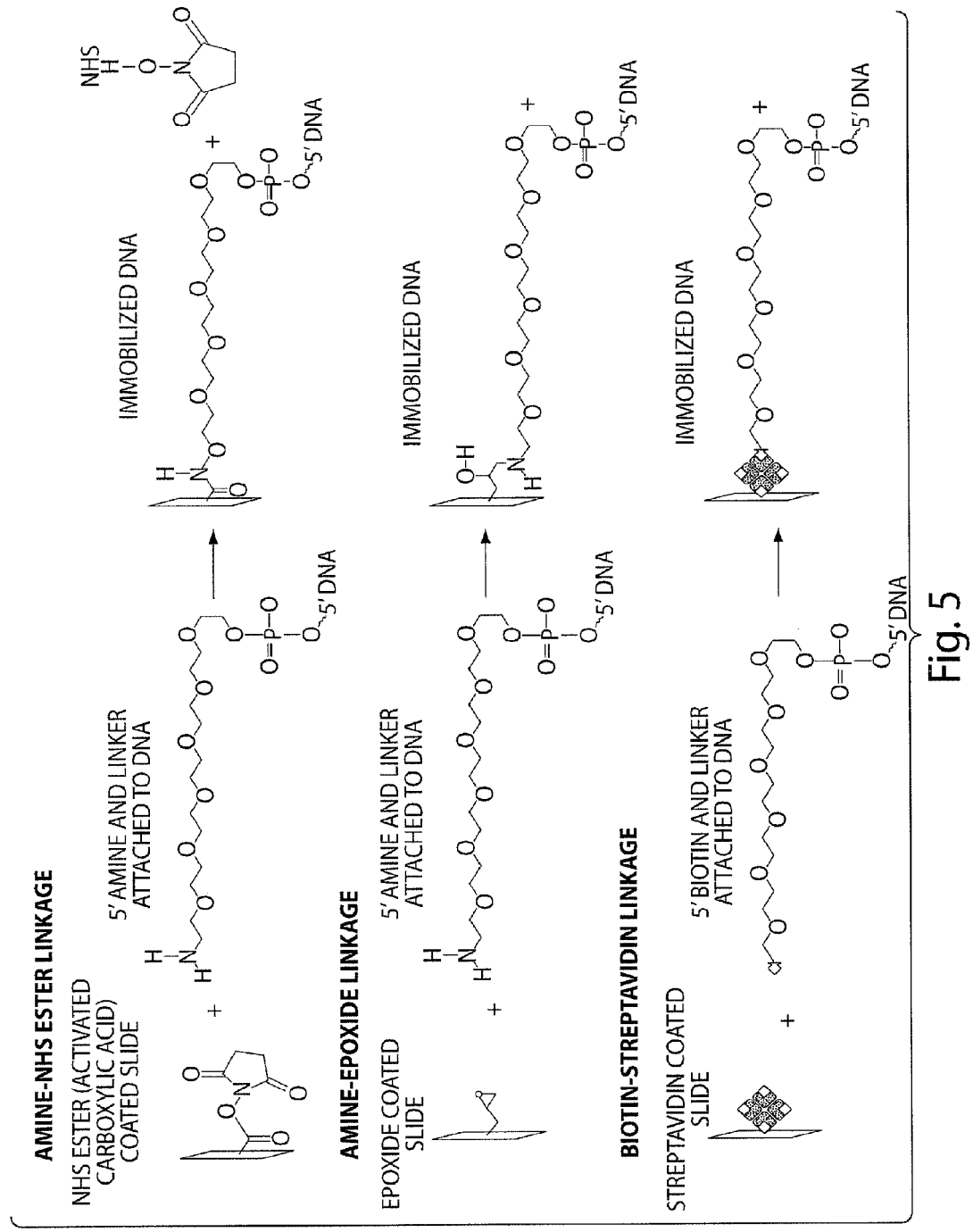
FIG. 5 is a schematic diagram of three possible template immobilization (or tethering) approaches.

Covalent chemistry is well understood within the field, with multiple possible chemistries available for attaching templates to solid supports. These solid substrate-templates chemistries include without limitation aminated substrate and phosphorylated DNA (Joos et al. *Anal Biochem* 247, 96-101 (1997)), aminated substrate and carboxylated DNA (Rasmussen et al. *Anal Biochem* 198, 138-42 (1991)), phosphorylated substrate and aminated DNA (Ghosh et al. *Nucl Acids Res* 15, 5353-5372 (1987)), carboxylated substrate and aminated DNA (Ghosh et al. *Nucl Acids Res* 15, 5353-5372 (1987)), epoxide-modified substrate and aminated DNA (Lamture et al. *Nucl Acids Res* 22, 2121-5 (1994)), isothiocyanate-activated substrate and aminated DNA (Guo et al. *Nucl Acids Res* 22, 5456-5465 (1994)), aldehyde-activated substrate and aminated DNA (Schena et al. *Proc Natl Acad Sci USA* 93, 10614-9 (1996)), gold-coated substrate and thiol or disulfide modified DNA (Boncheva et al. *Langmuir* 15, 4317-4320 (1999)), aminosilane-modified substrate and thiol or disulfide modified DNA (Chrisey et al. *Nucl Acids Res* 24, 3031-3039 (1996)), 3-mercaptopropylsilane-modified substrate and thiol or disulfide modified DNA (Rogers et al. *Anal Biochem* 266, 23-30 (1999)), azide-modified substrate and alkyl-modified DNA (Rozkiewicz et al. *Chembiochem* 8(16), 1997-2002 (2007)), and alkyl-modified substrate and azide-modified DNA (Rogers et al. *Anal Biochem* 266, 23-30 (1999)). FIG. 5 provides a schematic representation of three of the possible tethering schemes that can be used in accordance with the invention.

2. Binding of Observable Moieties to Template

Typically, the template must be attached to an observable (or detectable) moiety on its free end. This moiety is intended to represent the free end of the template and thus its position and movement in the direction of the force indicates the length of the template. The observable moiety can be any number of moieties and the invention is not limited by its nature. The nature of the observable moiety will dictate the type of sensor or detector suitable to observe (or detect or monitor) changes in the length of the template. In some important embodiments, the observable moiety is a bead such as a microbead, and even more particularly such as a magnetic bead. In these embodiments, the sensor may be any optical sensor, including but not limited to a CMOS imaging sensor (or CMOS contact imager), as described in greater detail herein. Such a detection approach may require a light source but it is independent of the wavelength of such light. In another embodiment, the observable moiety is a luminescent or fluorescent particle and the sensor is a charged coupled device (CCD). It is to be understood that the observable moieties are however not so limited.

The size of the moiety will depend on how it is being detected. If it is size-based detection, as for example may occur with a CMOS contact imager, then a moiety on the order of microns should suffice. As an example, 1-5 μm beads would be sufficient. Beads of this size including 2.8 μm beads are commercially available for sources such as Bangs Laboratories.

The moieties can be attached to the template through a variety of methods and employing a variety of interactions, including but not limited to non-covalent interactions such as biotin/streptavidin, DIG/anti-DIG, and fluoroscein/anti-fluoroscein binding pairs, as well as covalent interactions, such as those discussed herein in relation to covalent immobilization of templates (or primers) to support surfaces.

As an example, the simplest methodology for modifying the 3' end of a nucleic acid is an end-labeling process that is known and routinely used in the art to place moieties on the 3' end of a nucleic acid. In an exemplary process, an enzyme is used that can incorporate modified dNTPs to the 3' end of the template. Examples of such enzymes include but are not limited to T4 kinase and terminal transferase. The modification incorporated into the template will then determine a suitable linking chemistry for attaching the moiety to the template. For example, biotinylated or digilated dNTPs can be incorporated at or near the 3' end of the template and streptavidin or anti-DIG conjugated moieties can be bound thereto respectively. As another example, amino allyl dNTPs (typically dUTP) can be incorporated at or near the 3' end of the template and moieties comprising complementary chemistries can be bound thereto as outlined herein. The observable moiety is attached to the template at a position that effectively represents the end of the template. The moiety is preferably attached to the final nucleotide in the template. However it can be attached to another nucleotide near the end of the template provided that no sequencing reactions occur from the template region between the position of the moiety and the true end of the template.

Another method involves ligation (i.e., covalent attachment) of an oligonucleotide containing one or more modified nucleotides to the 3' end of the template by single stranded ligases. Examples of single-stranded ligases include but are not limited to T4 RNA ligase and CircLigase™ ssDNA Ligase (EPICENTRE® Biotechnologies).

Another method uses standard DNA polymerase and natural dNTPs until the desired number of amplified copies is obtained and then replaces the natural dNTPs with modified dNTPs and allows one or more additional amplifications to occur. In this way, the most 3' one or more copies on the template comprise one or more attachment moieties. The modified dNTPs may comprise for example biotin, DIG, or amino allyl. One, two, three or all dNTPs may be modified, and they may be modified with the same or different moieties. In some instances, a first DNA polymerase may be used to incorporate natural dNTPs and a second DNA polymerase may be used to incorporate modified dNTPs. This approach is useful when it is preferable to perform the vast majority of amplification cycles as quickly and as accurately as possible and then switch to a slower and less accurate polymerase for incorporation of the modified dNTPs. It may also be preferable where the first DNA polymerase has less affinity and/or reduced capacity for modified dNTPs. As an example, the first DNA polymerase may be Phi-29 or a similar enzyme that exhibits a reduced capacity to incorporate modified dNTPs. In these instances, the first DNA polymerase may be inactivated through a brief incubation at an increased temperature (e.g., in the case of Phi-29, an incubation at 40° C. to 50° C.), followed by the addition of the second DNA polymerase (e.g., Bst or Klenow) together with the modified dNTPs and other reagents.

Still another method for attaching observable moieties such as beads to the end of RCA products is through the use of the chain terminating nucleotide analogue AZT. In this method, the RCA product is terminated with AZT (i.e., the last residue incorporated into the RCA product is AZT). AZT contains a 3' azido group that can be reacted with and thus conjugated to other groups such as alkynes. Thus, an RCA product having an AZT at its end can be conjugated to a bead that is attached (preferably covalently) to an alkyne group. This type of click chemistry can be carried out at room temperature and preferably in the presence of a Cu catalyst such as but not limited to copper sulphate ($CuSO_4$). An example of such a reaction is described by Danel et al. *Bioorganic & Med Chem.*, 16:511-517 (2008).

Figure 9A:
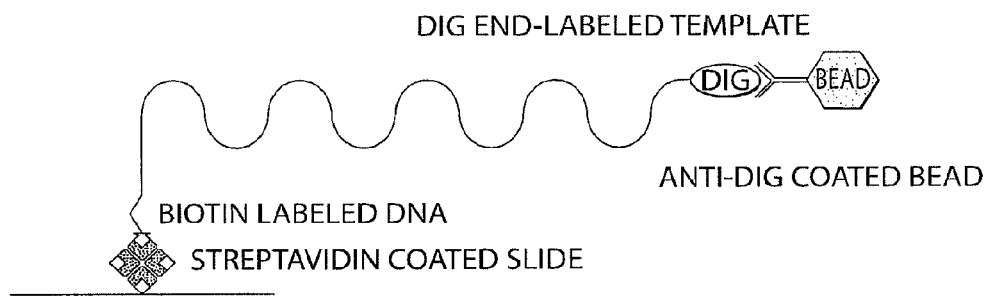
FIGS. 9A-C illustrate three possible immobilization strategies for templates and observable moieties.
Figure 9B:
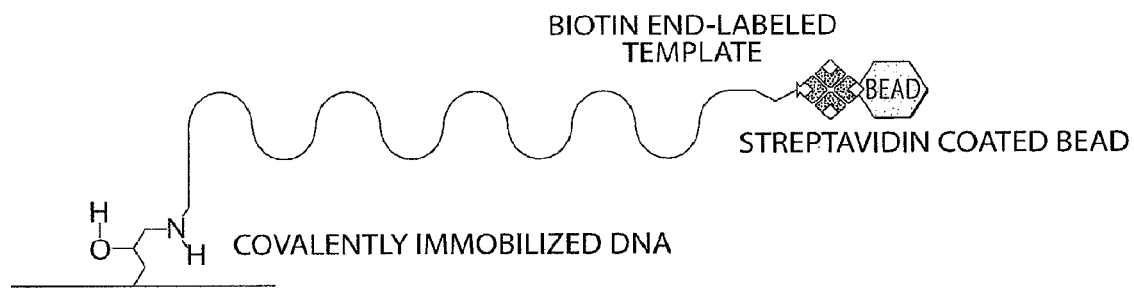
Figure 9C:
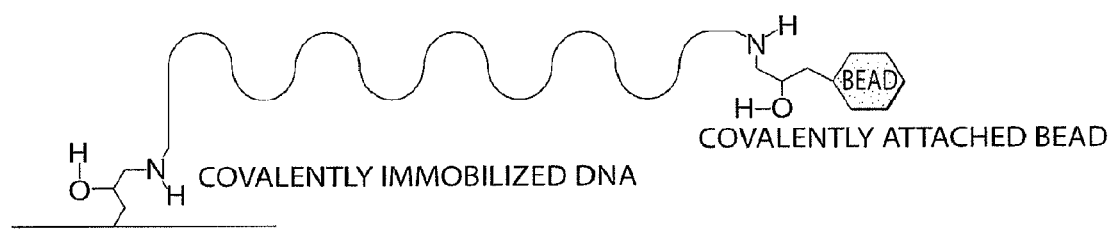

FIGS. 9A-C illustrate three non-limiting strategies that can be used to attach the template to the support surface (such as a glass slide) and the observable moiety (such as a bead) to the template. These strategies are (A) non-covalent interactions for template attachment to the support surface and non-covalent interactions for observable moiety attachment to the template (e.g., biotin/streptavidin for template immobilization and DIG/anti-DIG for the observable moiety attachment), (B) covalent template attachment to the support surface and non-covalent attachment of observable moiety to the template, and (C) covalent attachment of template to support surface and covalent attachment of observable moiety to template.

3. Flow Cell

The solid support is part of or adjacent to a flow cell. As used herein, a flow cell is a chamber having at least an inlet and an outlet port through which a fluid travels. The solid support to which the template is tethered may be below, above or beside the flow cell, depending on the position of the detection system used to observe the template. The solid support may be a wall of the flow cell including a bottom wall, a side wall, or a top wall.

Figure 3:
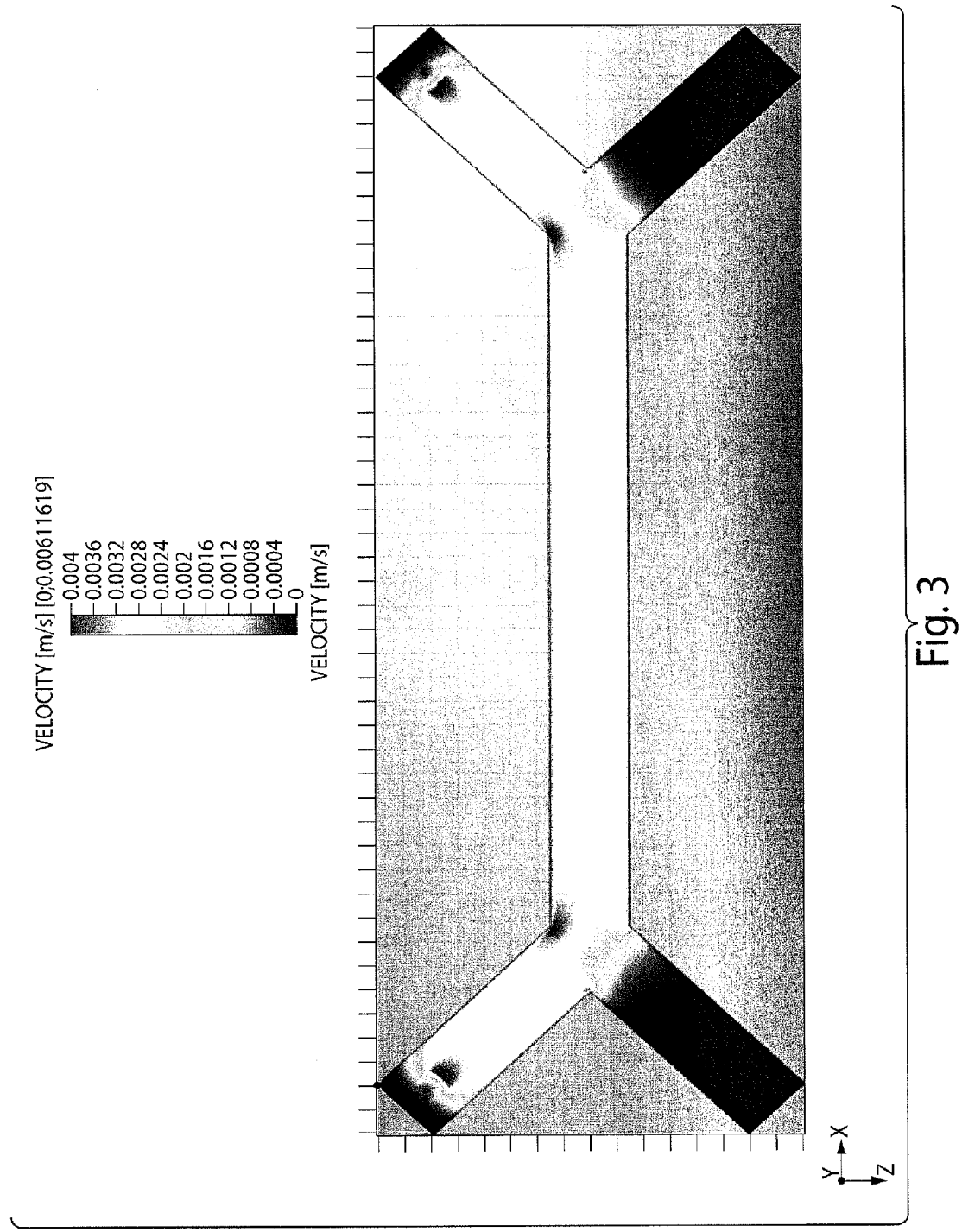
FIG. 3 is a Finite Element Analysis model of a 4 ml/h flow of liquid through a flow cell that is 125 μm deep and 3 mm wide.
Figure 4:
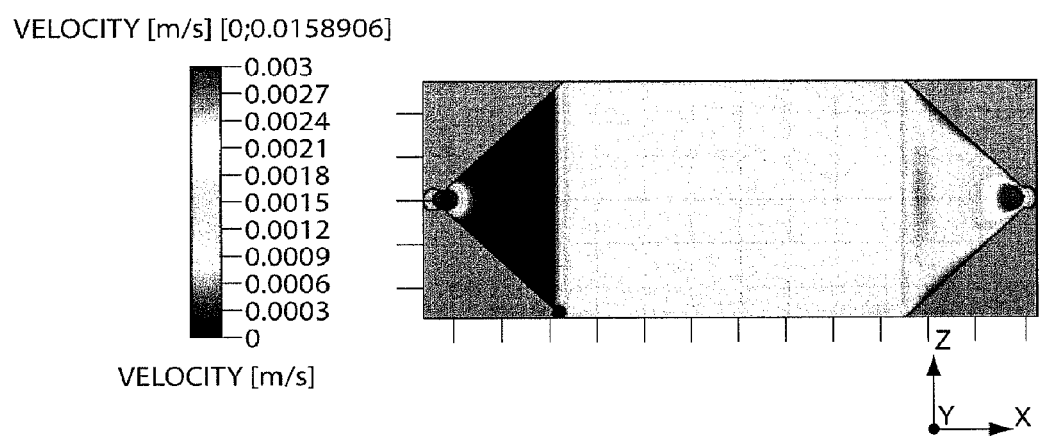
FIG. 4 is a Finite Element Analysis model of a 4 ml/h flow of liquid through the redesigned flow cell 100 μm deep that has a 5.5 by 7 mm flow surface for laminar flow over the entire field of view of 4.8 by 6.4 mm.

The invention provides a flow cell to be used together with the solid support. The flow cell is designed with dimensions that provide a uniform flow regime over a large area. As a comparison, FIG. 3 represents the flow cell described by van Oijen et al. *Science* 301, 1235-8 (2003). The surface area of this flow cell is significantly larger than the field of view (1.78 mm×2.37 mm) and this renders it unsuitable for simultaneously tracking multiple fields of view during reactions characterized by rapid changes in reagents, such as those contemplated by the invention. One embodiment of the flow cell provided by the invention is shown in FIG. 4. This flow cell has been designed to minimize the dead volume outside the field of view (4.8 mm×6.4 mm) while maintaining laminar flow across the entire field of view. This allows rapid changing of reagents at appropriate flow rates, and this reduces cycling times for sequencing.

Flow cell dimensions may be governed by the limitations of the detection systems used. For example, for embodiments using a charged coupled device (CCD), the flow cell dimensions will be governed by the width and length of the CCD divided by the magnification used. In addition, in order to guarantee fully developed flow in the full field of view (i.e., the part of the flow cell observed by the camera, as an example), about 1 mm is added to the sides of the flow cell (e.g., 0.5 mm on each side) parallel to the flow direction and 1 mm to each side perpendicular to the flow direction. The flow cell height is selected such that flow velocity roughly increases linearly with distance from the surface.

The flow cell of the invention also permits a greater density of templates to be immobilized on the solid support at an axis perpendicular to the flow, and stretched simultaneously without steric interference. Under non-uniform flow directions in the flow cell, templates must be oriented and spaced apart from each other sufficiently so that none interferes with any other template. This in effect requires that each template be surrounded by an area of a circle having a radius that is equal to or greater than the maximum length the template can achieve during a sequencing reaction under tension. The area of a circle is required when the flow is non-uniform and the template may be oriented in essentially any direction.

The maximum number of samples (or templates) that can be analyzed in a given view therefore depends on the area of each circle demarcated by the tethered template. For example, assuming that a double stranded 50 kb template can assume a length of 20 then each template will require at least a 20 μm radius circle around it to avoid interference from other templates. The maximum number of templates (and thus samples) that can be accommodated on, for example, a 1 mm×1 mm image space is therefore on the order of 723, which exceeds the number of molecules previously simultaneously reported (van Oijen et al. *Science* 301, 1235-8 (2003)).

If on the other hand the flow is uniform in one direction, then less space is needed around each of the templates since all the templates will extend in only one direction. Thus under uniform flow conditions, the free space conformation (i.e., the space around each tethered template that cannot be occupied by another template) can be changed from a circle to a rectangle, where the length of the rectangle is determined by the maximum template length, and the width is determined by the degree to which the template is expected to arch while being stretched. In some embodiments, a width on the order of about 5 μm on either side of the tethering point should be suitable. Thus if the samples are packed in rectangular conformation with a 20 μm distance between events in the direction of the flow, but a 10 μm distance (i.e., 5 μm on either side of the tethering point) separating tethered molecules in the axis perpendicular to the flow, the maximum number of events in a 1 mm×1 mm space increases to 1000 (where maximum number of events means maximum number of templates that can be observed). Based on these numbers, increasing the resolution of the CCD camera beyond 0.6 megapixel directly increases the theoretical maximum number of events that can be monitored, as shown in Table 1. Table 1 also shows dimensions of representative surfaces that can be used for immobilization of templates. The number of monitored events can also be substantially increased beyond those obtained in the prior art by modifying the system to include an automated motorized microscope stage with image tiling software. This has been used successfully for microarray systems that employ fluorescent microscopes for imaging (Pihlak et al. *Nat Biotechnol* 26, 676-84 (2008)). Application of this imaging technology to the methods described herein would expand the 1 mm$^2$ reaction surface area previously monitored (van Oijen et al. *Biopolymers* 85, 144-53 (2007)) to 48 by 36 mm$^2$.

The invention contemplates other strategies for increasing the density of templates tethered to the solid support. For example, maximally efficient packing can also be achieved through creation of ordered arrays. In one instance, processes such as self-assembling arrays (Yan et al. *Science* 301, 1882-4 (2003)) utilize biotin interactions to generate features on solid supports, such as uniform-width nanoribbons and two-dimensional nanogrids. In another instance, photolithography can be used to create small regions on the solid support to which only a single molecule is attached. The single molecule may be a primer or it may be an entity that binds to a primer such as but not limited to a protein. In still another instance, periodic diffusion barriers in supported bilayers can be used to provide highly regular and densely packed arrays of flow-stretched DNA (Visnapuu et al. *Langmuir* (2008); Fazio et al. *Langmuir* 24, 10524-31 (2008)).

In still other embodiments, primers may be synthesized directly onto the solid support. This can be accomplished using any of the processes known in the art, as exemplified by Maskos et al. (*Nucleic Acids Res* 20, 1675-8 (1992)). A non-comprehensive, non-limiting list of exemplary processes includes in situ synthesis via ink-jet printing delivery of phosphoramidites (Blanchard et al. *Biosens Bioelectron* 11, 687-690 (1996)), parallel synthesis directed by individually electronically addressable wells (Egeland et al. *Nucl Acids Res* 33, e125 (2005)), maskless photo-generated acid (PGA) controlled synthesis (Gao et al. *Nucl Acids Res* 29, 4744-50 (2001); LeProust et al. *J Comb Chem* 2, 349-54 (2000)), mask directed synthesis utilizing photolithography (PLPG) (Fodor et al. *Science* 251, 767-73 (1991)), and maskless PLPG parallel in situ synthesis (Singh-Gasson et al. *Nature Biotechnology* 17, 974-978 (1999)).

If only one primer (on average) is used for extension, the array will be ordered but not completely occupied. While still useful in the invention, it is preferable to use high occupancy, ordered arrays. This can be achieved for example by placement of large molecules that contain only a single primer and that once bound to an activated region of the solid support exclude the binding of other molecules (for example due to size).

The devices and methods provided herein do not depend on physically separating polymerase-mediated extension reactions from each other, as is the case with some prior art sequencing methods that depend upon detection of sequencing reaction products or byproducts such as inorganic phosphate. These prior art methods typically use wells to to physically separate sequencing reactions from each other. The methods provided herein on the other hand can be performed even if the reaction products or byproducts are not physically segregated. Templates are therefore referred to herein as being "in fluid communication" with other templates, and regions on a solid support are referred to herein as being in fluid communication with other regions on the solid support. Such solid supports therefore do not have wells or microwells situated on them.

4. Microfluidics

The invention requires fluid flow over the immobilized templates. Flow into and through a flow cell may be controlled by pumps through a valve block, either or both of which may be computer controlled. In some embodiments, the pumps provide only a single reagent such as a single type of nucleotide selected from dATP, dCTP, dGTP and dTTP, or such as the wash buffer and/or apyrase. In one embodiment, the flow cycle is wash buffer, dATP, apyrase, wash buffer, dCTP, apyrase, wash buffer, dGTP, apyrase, wash buffer, dTTP, apyrase, and wash buffer. Length measurement can occur prior to, at the same time as, or after apyrase flow or prior to, at the same time as, or after wash buffer flow. In any event, it has to occur before the flow through of the next dNTP(s). In other embodiments, two or three of the nucleotides may be combined and flowed into the flow cell together with the remaining nucleotide(s) flowed in separately. The data resulting from such syntheses will be discussed in greater detail herein. FIG. 2 provides a schematic representation of an embodiment of the system of the invention illustrating the relative arrangement of pumps, reagent reservoirs, solid supports (referred to as a "bead array"), detection apparatus (e.g., CCD camera on a microscope), and waste reservoir. The computer may be a personal computer, a work station, a networked computer, a distributed computing system, and the like, as will be appreciated by those of ordinary skill in the art.

Accurate, reproducible measurement of DNA length while under tension, such as is contemplated by the invention, can be compromised by variations in the flow rate (van Oijen et al. *Biopolymers* 85, 144-53 (2007)) used to provide the tensioning force. The syringe pumps typically used to drive flow rates in the prior art have been shown to introduce variation (Lindberg et al. *Cytometry* 16, 324-330 (1994)) and inaccuracy (Weiss et al. *Can J Anesth* 47, 1031-1035 (2000)). In contrast, gas-driven pneumatic systems that provide pressure-driven flow control using helium, argon or another inert gas appear less susceptible to such variation and inaccuracy (Braschler et al. *Lab Chip* 7, 420-2 (2007)).

An additional advantage of pneumatic systems is that they can be easily interfaced with manifold valves integral to the flow cell, providing the ability to rapidly switch between reagents flowing into the flow cell and across the surface of the solid support. This rapid switching is achieved by flowing concentrated reagents into a continuous stream of buffer. Short flow paths between valves resulting in smaller "dead" volumes and microfluidic mixing individually and together facilitate rapid change-over between reagents. The transient flow rate changes are dampened with compliant tubing between the valve manifold and the flow cell. In addition, degassing of the reagents is prevented by operating the flow cell at high pressure. This is achieved with a flow resistor at the outlet of the flow cell. This type of arrangement has significant advantages over syringe pumps particularly with respect to the rates at which reagents can be changed, thus ultimately increasing the rate at which the sequencing reaction can occur. Using the flow cells and pneumatic valve systems as described herein and examples of which are provided below, reagent cycling can occur in as little as 1 second, resulting in a 60 second sequencing cycle (i.e., the flow through and wash of all four nucleotides), and approximately a 3.5 hour sequencing run that is 200 cycles long.

Figure 6:
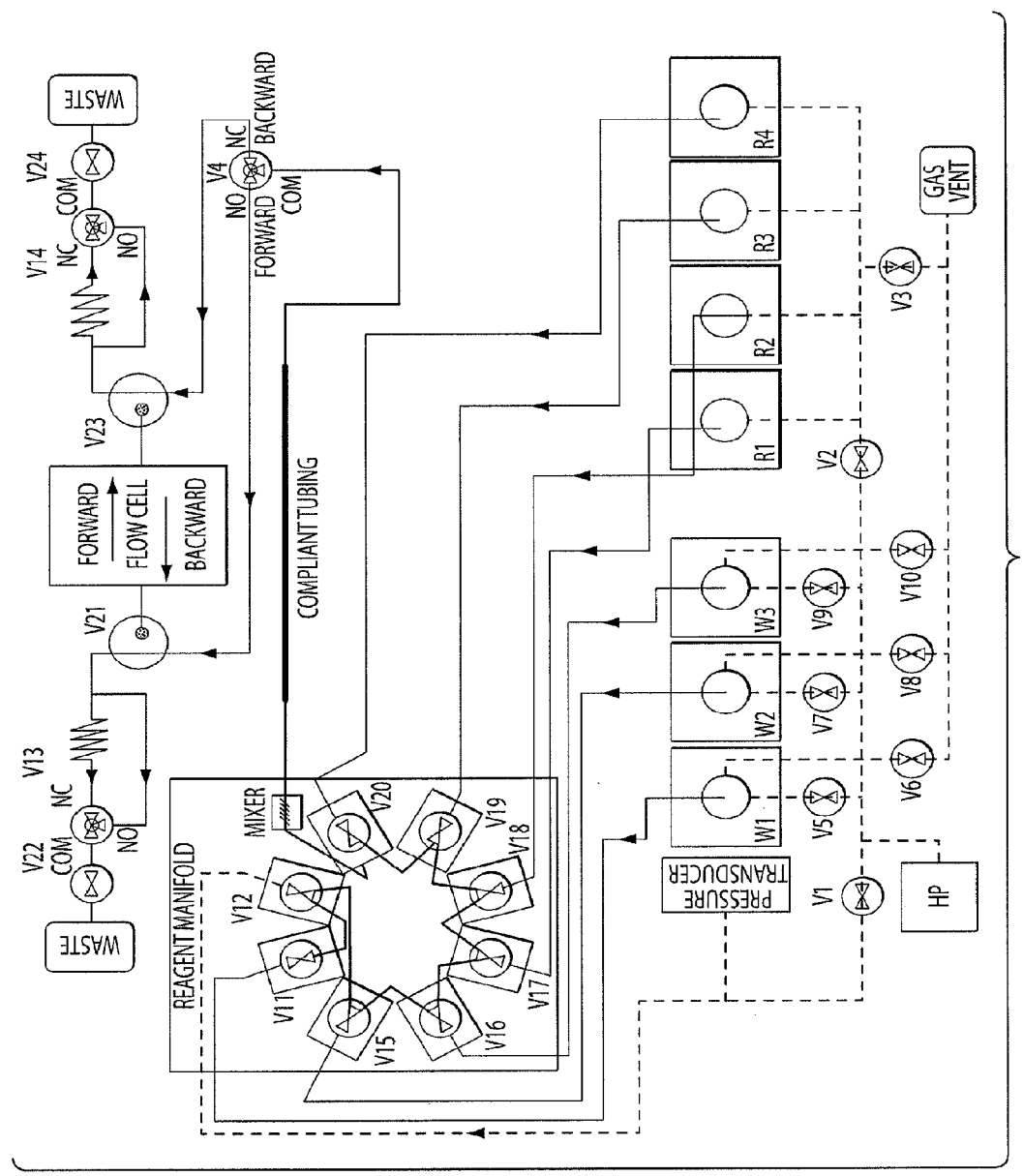
FIG. 6 is a schematic of a microfluidics system contemplated by the invention.

The fluidics system is shown schematically in FIG. 6. Four nucleotides (represented as reagents 1-4) and three washing solutions (represented as W1 for the instrument cleaning solution, W2 for the buffer for continuous operation, and W3 for the nucleotide wash accelerant such as apyrase) are pressurized using the same pressure source (e.g., nitrogen, argon, helium, or other inert gas). The wash solutions may be individually pressurized using separate valves (valves V5, V7 and V9) whereas the reagents are pressurized using the same valve (V2). A circular arrangement (preferably on both sides of the manifold) allows the flow of buffer (W2) with selective introduction of either W3, R1, R2, R3 or R4. The flow direction over the solid support (which in FIG. 6 is a chip) can be selected by appropriate opening and closing of valves V13, V14, V4, V21, V22, V23 and V24. To prime reagents rapidly with high flow rates through the system, a low fluid resistance can be selected for either direction. The manifold includes a microfluidic flow mixer and appropriate tubing between the manifold, and the flow direction manifold introduces the appropriate compliance to dampen flow fluctuations due to opening and closing of valves.

Figure 7A:
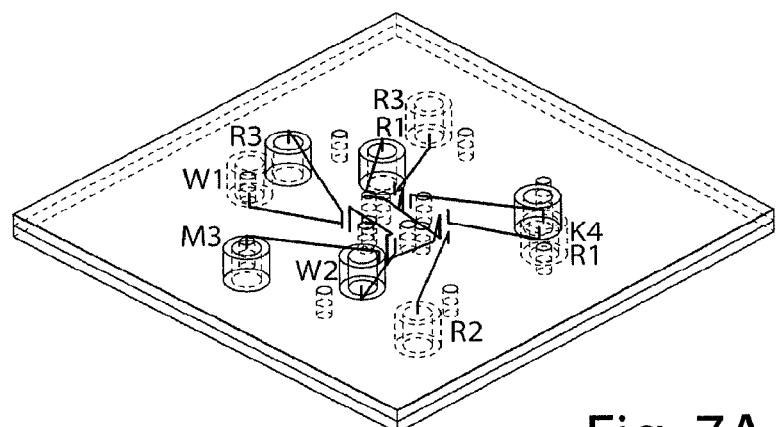
FIGS. 7A-B are schematics of the flow paths, valve block, and integrated system in microfluidic embodiments of the invention.
Figure 7B:
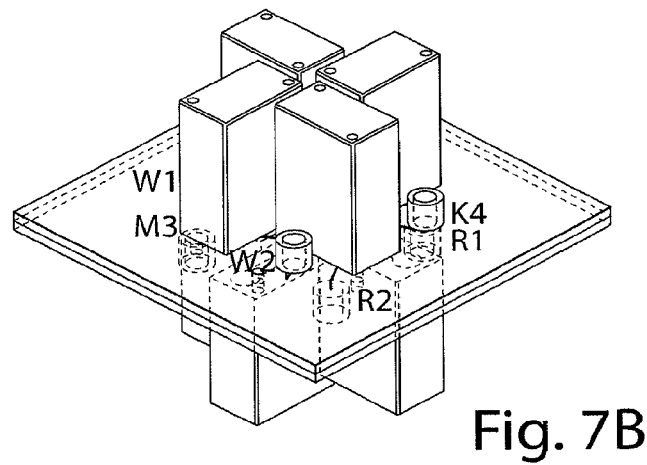
Figure 7C:
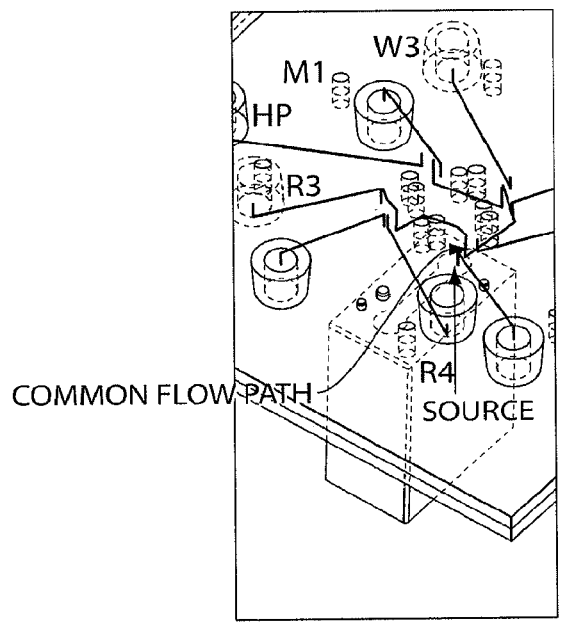

FIGS. 7A-C show a three dimensional model of one embodiment of the reagent manifold described herein. Of particular interest is the Burker 0127 series valve which introduces reagents to a common flow path by creating a flow chamber between the source and common path. When these valves are closed, there is near zero unswept dead volume, thus preventing contamination of common flow stream by the source.

As will be appreciated, accurate and rapid sequencing of the template is dependent on the extent to which and the rate at which unincorporated nucleotides are removed from the system. Thus, rapid and complete (or near complete) removal of unincorporated nucleotides is important. The microfluidic system must also be designed to maximize washing potentially resulting in smaller wash volumes and wash duration.

As will also be appreciated to those of ordinary skill, the rate of diffusion within the flow cell is effectively zero at any boundary layer (including at the surface of the solid support where the template is tethered). As a result, the rate of dNTP clearance (or removal) at this surface is extremely low relative to the rate of dNTP clearance from the center of the fluid flow (or flow cell). The shape of the flow cell will also affect clearance rates and efficacy. For example, it has been estimated that for cylindrical systems (or flow cells) three volume exchanges are needed to remove on the order of about 98% of the unincorporated dNTP, while for non-cylindrical systems (or flow cells) seven volume exchanges are needed to achieve the same degree of dNTP clearance. In one embodiment, the flow cell is a rectangle of very limited height or depth, akin to a rectangular slit.

Figure 8:
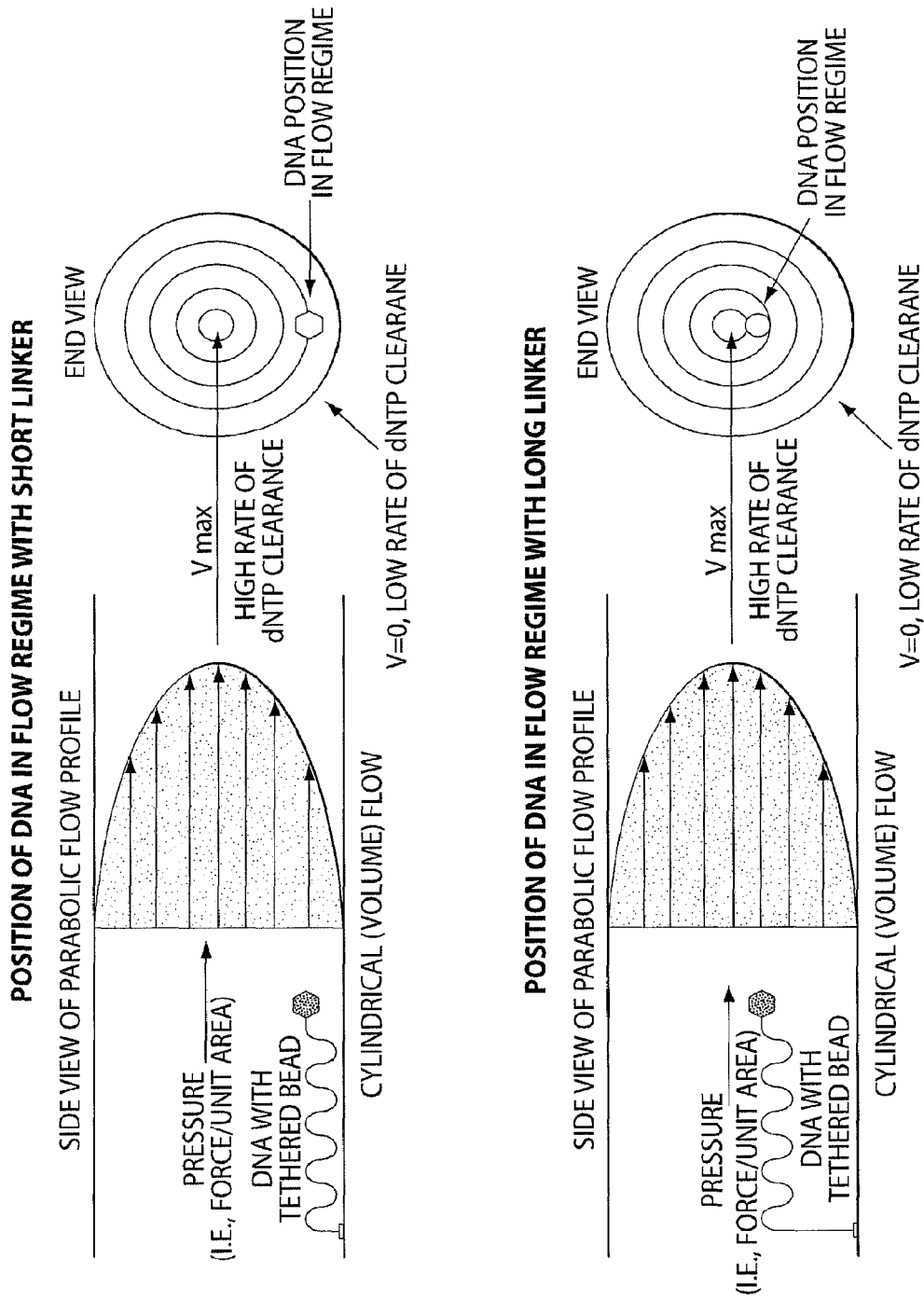
FIG. 8 illustrates the positioning of the template above the surface of the flow cell and the effect of increased linker length.

One way of addressing this issue is to distance the template from the surface by introducing a linker (or spacer, as these terms are used interchangeably and are understood in the art) between the surface and the template (i.e., attaching the template to the surface indirectly via the linker). Moreover, the linker length may be increased or extended sufficiently to position the template away from the surface. This is illustrated in FIG. 8. In some embodiments, the bead position is at about 1-15% or 1-5% of the total flow cell height from the surface, as it is these regions in the flow cell in which there is a linear relationship between height and flow velocity. The bead position may also be at about 10-20% of the total length of the molecule.

The spacers may be any of those known in the art provided they are inert to the various reaction substrates, enzymes and products used in the reactions of the invention. A suitable linker is polyethylene glycol (PEG). Various types of other commercially available linkers are reactive with one or more of the following groups: primary amines, secondary amines, sulphydryls, carboxyls, carbonyls and carbohydrates. Examples of amine-specific linkers are bis(sulfosuccinimidyl)suberate, bis[2-(succinimidooxycarbonyloxy)ethyl]sulfone, disuccinimidyl suberate, disuccinimidyl tartarate, dimethyl adipimate.2HCl, dimethyl pimelimidate.2HCl, dimethyl suberimidate.2HCl, and ethylene glycolbis-[succinimidyl-[succinate]]. Linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Linkers preferentially reactive with carbohydrates include azidobenzoyl hydrazine. Linkers preferentially reactive with carboxyl groups include 4-[p-azidosalicylamido]butylamine. Heterobifunctional linkers that react with amines and sulfhydryls include N-succinimidyl-3-[2-pyridyldithio]propionate, succinimidyl [4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxylhydrazide.2HCl, 4-(4-N-maleimidophenyl)-butyric acid hydrazide.2HCl, and 3-[2-pyridyldithio]propionyl hydrazide.

Clearance of unincorporated nucleotides can also be facilitated in part or in whole through the use of apyrase which degrades unincorporated dNTPs and renders them unsuitable for further incorporation. The apyrase may be free flowing, added to the wash buffer, and introduced into the flow cell once incorporation of any given nucleotide triphosphate type has ceased (as indicated by the cessation of any above-background movement by the detectable moiety at the end of the template). Alternatively or additionally, apyrase may be fixed or immobilized within the flow cell such as for example to the solid support surface (to which the template is also fixed or immobilized). This may occur through the use of a linker in order to make the enzyme more accessible and to remove any steric hindrance relating to close proximity to the surface. Apyrase may be attached to a variety of linkers that differ in length. In this way, apyrase may be present in a variety of flow streams within the flow cell, including those closer to the walls and those that are closer to or at the center flow streams. As discussed above, it is the flow streams near the walls which travel with low velocity and unincorporated dNTPs present in these flow streams are less likely to be cleared away. Having apyrase in these flow streams should improve removal of these dNTPs. This will increase the likelihood that changes in template length are a result of incorporation of a dNTP newly introduced into the flow cell rather than a residual and unincorporated dNTP that remains in the flow cell after washing.

Another important consideration in achieving efficient incorporation and accurate measurement of changes in template length is to prevent interaction of the template or the observable moiety on the end of the template (e.g., a magnetic bead) with the solid surface. Interactions between the surface and the template or the moiety, whether they be ionic, physical or otherwise, may inhibit the free movement of the template or moiety, and thereby interfere with monitoring of the template and moiety. This can be avoided in a number of ways. For example, such interactions can be reduced or prevented altogether by coating the solid surface with a layer of passivating molecules. Suitable passivation molecules include inert polymeric materials such as but not limited to polyethylene glycol (PEG) or highly branched dextran (Floyd et al. *PNAS* 105:15382 (2008)), polyvinylpyrrolidone (PVP), Ficoll or bovine serum albumin (BSA), for example. PEG of various molecular weights can be used including but not limited to PEG-8000 (8 kDa), PEG-12000 (12 kDa), or PEG-20000 (20 kDa). Coating of the solid support can be accomplished by any of the covalent or non-covalent linking methods discussed herein, or by dynamic passivation by adding the passivation molecules to all flowthroughs including reagent flowthroughs and washes.

Passivation efficiency can be increased through the use of longer chain PEG, including for example 40 kDa PEG (Jen-Kem Technology USA Inc., Allen, Tex.), as well through the use of linear and/or branched 10-30 kDa PEG (NOF Corporation, Tokyo, Japan). The PEGs may be functionalized such as heterobifunctional derivatives. Such derivatives can then be attached to other molecules useful in the reactions and/or washes. As an example, two or more types of PEGs of differing lengths could be applied to the solid support, providing a lawn of shorter PEGs with interspersed longer PEGs at a frequency determined by both the relative binding efficiencies and respective molecular concentration (or ratios) of the two PEGs.

In one embodiment, apyrase may be conjugated to one of the immobilized PEG populations. In this way, apyrase may be continually present to degrade unincorporated residual dNTPs thereby potentially reducing wash volumes and times between cycles. Clearly dNTPs are provided in concentrations sufficient to allow maximum incorporation even in the presence of the tethered apyrase. In another embodiment, oligonucleotide primers could be conjugated to one or more of the PEG populations to permit subsequent target or template binding. In still other embodiments, polymerases used in the sequencing reactions may be conjugated to one or more of the PEG populations. In still other embodiments, a variety of molecules could be attached to a single support surface via the different PEG populations. As an example, apyrase could be provided attached to 8 kDa PEG, oligonucleotide primers could be provided attached to 40 kDa PEG, and both types of PEG could be immobilized on the same surface resulting in a mixed functionality surface.

An alternative method of reducing interactions between the surface and an observable moiety that is a magnetic bead is the application of a magnetic field that exerts a small (e.g., typically 1 pN or less) force to the bead in the upwards direction, away from and perpendicular to the surface and the flow (Lee et al. Nature 440:246-9 (2006)). The upward force is small in comparison with the horizontal drag force, resulting in a stretching of the template predominantly in the horizontal direction, leaving unaffected the ability to measure its length by tracking bead position. The small upward force will be large enough, however, to lift the bead away from the surface to prevent any interaction between it and the surface. As will be appreciated, this approach also moves the template into more centralized stream lines and flows within the flow cell, thereby capitalizing on the higher solution velocity, increased effective flow and thus stability offered by this position in the flow cell.

5. Sequencing Reaction

In some aspects of the invention, the sequencing methods are referred to as sequencing-by-synthesis reactions. This means that determining the sequence of a first nucleic acid requires the synthesis of a second nucleic acid using the first as a template. In this way, the sequence of the second nucleic acid is determined from the order and number of incorporated dNTPs, and the sequence of the first nucleic acid is determined as the complement of the first nucleic acid sequence. The methods of the invention detect dNTP incorporation by a change in length of the template and not be directly observing the addition of the dNTP to nucleic acid being synthesized. As a result, the dNTP can be natural dNTP (i.e., dNTP that lack any modification including any exogenous detectable label such as a fluorophore). As should be clear from this disclosure, the sequencing methods of the invention also require that the template remains intact.

Some aspects of the invention involve sequencing methods that are described as occurring in the absence of fluorescence or in a non-fluorescent manner. These characterizations mean that the methods can be carried out without detection of fluorescence, particularly without detection of fluorescence from each incorporated dNTP. Embodiments of these methods therefore may employ natural dNTPs that have not been modified by addition of an exogenous fluorophore. These characterizations do not exclude however the possibility that the observable moiety conjugated to the free end of the template is itself fluorescent. In this latter instance, changes in the length of the template may be visualized via the fluorescence of the observable moiety rather than any fluorescence from individually incorporated dNTP.

Similarly, it will also be understood that the sequencing methods provided herein are able to detect nucleotide incorporation by detecting the observable moiety itself (e.g., as is possible with a CMOS contact imager). Thus, in some embodiments, the observable moieties are detected directly and without the need for an enzyme-mediated event. An example of enzymatically detected nucleotide incorporation is pyrosequencing coupled with sulfurylase and luciferase mediated detection of released inorganic pyrophosphate. (See Leamon and Rothberg, *Chemical Reviews*, "*Cramming More Sequencing Reactions onto Microreactor Chips*", 2006.) Thus, aspects of the invention are referred to as non-enzymatic methods (or as detecting nucleotide incorporation non-enzymatically) since nucleotide incorporation can be detected in the absence of enzyme-generated signals.

The invention contemplates performing a plurality of different sequencing reactions simultaneously within the same flow cell or on the same solid support. Each sequencing reaction yields information about one template immobilized on the solid support. The number of templates that can be sequenced in a single run will depend on the expected length of the template and the area of the solid support. Therefore depending on the embodiment, at least 100, at least 200, at least 300, at least 400, at least 500, at least 600, at least 700, at least 800, at least 900, or at least 1000 templates may be immobilized on a solid support and thus sequenced simultaneously. In still other embodiments, 100-500, 100-750, 100-1000, 500-1000, 600-1000, 700-1000, 800-1000, 900-1000, 1000-2000, 2000-3000, 3000-4000, 4000-5000, 5000-10000, or more templates may be sequenced simultaneously. Table 1 shows that the solid support can be configured to have 1.6 pixels per 2.8 μm bead.

The sequencing reaction is carried out by incorporating dNTPs into a newly synthesized nucleic acid strand that is hybridized to the template. The newly synthesized strand may derive from a primer that is bound to the template or from other molecule from which polymerase-mediated extension can proceed. The primers may be hairpin primers.

In one non-limiting example, the sequencing reaction may be commenced by contacting templates with primers under conditions that permit their hybridization, and contacting template/primer hybrids with polymerases. Such contacting may occur before, during and/or after immobilization to the solid support. In an important embodiment, it occurs following immobilization to the solid support.

Once the primers and polymerases are bound to the template, repeated cycles of reagents are flowed into and through the flow cell. When the reagent flow contains a nucleotide that is complementary to the nucleotide on the template that is directly downstream of the 3' end of the primer, the polymerase will incorporate the dNTP. If contiguous downstream positions on the template are occupied by identical nucleotides (referred to herein as a homopolymer), the polymerase will incorporate an identical number of complementary dNTPs. Such incorporation will cease when the dNTP in flow is not complementary to the next available nucleotide on the template. The amount of flowed dNTP and the time of such flow will respectively exceed the number of complementary bases on the template and the time needed to incorporate all possible dNTPs.

Importantly, incorporation of the complementary dNTPs occurs at more than one of the bound primers. More preferably, incorporation occurs at least 10%, at least 25%, at least 50%, at least 60%, at least 70%, at least 80%, at least 90%, or at all of the bound primers. The percentage of primers may depend upon the number of target copies in the template. For some embodiments, incorporation occurs at least 30, at least 35, at least 40, at least 45, at least 50, at least 60, at least 70, at least 80, at least 90, at least 100 or more primers per individual template. It will be understood that the invention contemplates incorporating dNTPs at as many of the hybridized primers on a given template in order to increase signal to noise ratio by increasing the magnitude of the length change that occurs (whether it is an increase or decrease in length).

As part of the sequencing reaction, a dNTP will be ligated to (or "incorporated into" as used herein) the 3' of the newly synthesized strand (or the 3' end of the sequencing primer in the case of the first incorporated dNTP) if its complementary nucleotide is present at that same location on the template nucleic acid. Incorporation of the introduced dNTP converts a single stranded region of the template into a double stranded region, and this conversion is then reflected in a change in length of the template under tension. The change in length is detected by determining and monitoring the position of the observable moiety (e.g., a bead) located at the free end of the template. Therefore, if the bead position is unchanged after any given flow through, then no dNTPs have been incorporated and one can conclude that the flow through dNTP was not complementary to the next available nucleotide in the template. If a change in position of the moiety is detected, then the flow through dNTP was complementary and was incorporated into the newly synthesized strand. dNTPs may be flowed in any order provided the order is known and is preferably kept constant throughout the sequencing run.

The targets may be engineered to render a template having an additional known nucleotide sequence just 3' of the hybridized primer. This sequence is referred to herein as a test or "key" sequence. This known sequence should then be the first sequence to read out in a sequencing reaction and it can be used to as an internal standard to confirm that correct dNTP incorporation is occurring. These early incorporation events can also be used to locate the observable moiety and to determine the extent of movement per incorporation event for each template. In these embodiments, the sequence may be identical between templates. The sequence can also be used to denote information about the template (and thus usually the target also). For example, it can be used to denote the source of the target and/or conditions used to amplify the target. In these embodiments, the sequence may differ between templates. The length of the sequence may be 2, 3, 4, 5, 6, 7, 8, 9, 10, 15, 20, or more nucleotides.

As the template/primer hybrid becomes increasingly double-stranded with every nucleotide incorporation, the template length changes. If the force applied to the template is less than 6 pN, then the template lengthens with each incorporation. If the force is greater than 6 pN, then the template shortens with each incorporation.

In some embodiments, the invention contemplates using forces ranging from about 0.5 pN to about 12 pN, preferably about 0.5 pN to about 10 pN. In some embodiments, the force is about 0.5 pN, about 0.6 pN, about 0.7 pN, about 0.8 pN, or about 0.9 pN, about 0.5 pN to about 1 pN, about 0.6 pN to about 1 pN, about 0.7 pN to about 1 pN, about 0.8 pN to about 1 pN, or about 0.9 pN to about 1 pN. In some embodiments, the force can be about 1 pN, about 2 pN, about 3 pN, about 4 pN, about 5 pN, about 6 pN, about 7 pN, about 8 pN, about 9 pN, about 10 pN, about 11 pN, or about 12 pN. In some important embodiments, the force is about 2 pN to about 3 pN. Polymerase activity will be unaffected by the forces contemplated by the invention.

As used herein, a template that has a force exerted upon it is referred to herein as being "under tension". The force may be applied in a step wise fashion or through a gradually increasing force until the desired force is reached. Typically, the templates will be under the desired force during the extension (or incorporation reactions). Alternatively, the force may be applied during a wash or apyrase flow through, and the extension reaction may occur in the absence of force (or at least in the absence of sufficient force to extend the template sufficiently for purposes of the invention). As stated herein, if the force is greater than 6 pN but less than about 12 pN, then templates will decrease in length with nucleotide incorporation while if the force is less than 6 pN, then templates will increase in length with nucleotide incorporation.

The change in length of the template is monitored by observing the position of the observable moiety and/or determining the distance it moves after any given dNTP flow through. The position of all of the tethered observable moieties within the field of view are captured by a detector or sensor such as a CCD camera or a contact imager and then stored to a computer for further algorithmic analysis. The relative position of the moiety following each and every dNTP flow is then matched to the dNTP in each respective flow, and in so doing the sequence of the template is determined. No change in template length is expected during washes.

The invention contemplates the generation of fine and gross sequencing information useful for assembly of individual nucleic acid fragments, assembly and orientation of larger contigs such as those used in large scale sequencing analyses, or assembly or complete genomic sequences from smaller sequenced fragments. In the past, optical maps (Schwartz et al. *Science* 262, 110-4 (1993); Miller et al. *Am Biotechnol Lab* 9, 10 (1991); Johnson et al. *Genet Anal Tech Appl* 8, 75-6 (1991)) have proven a valuable tool to aid genomic assemblies. The methods and systems described herein can be used to detect the same type of orienting patterns or landmarks in a genome as detected in known sequencing methodologies in a manner completely compatible with the various data output.

In one aspect, the invention contemplates combining three of the four nucleotides and flowing that combination through the flow cell with the remaining nucleotide flowed through separately. As an example, one flow would include dATP, dCTP and dGTP while the other separate flow would include dTTP. During the flow through of the combined dNTPs, primers would be extended up to adenine residues on the template, in this particular example. Nucleotide incorporation would only occur at adenine residues when dTTP is flowed through. This process will generate a map indicating the presence of adenine residues on the template (or conversely incorporation of dTTP into the newly synthesized strand) compared to the presence of the remaining residues (i.e., cytidine, guanine or thymidine residues in the template, or conversely incorporation of dGTP, dCTP or dATP, respectively, into the newly synthesized strand). This can also generate a map of the length and position of sequence without adenine homopolymers and a map of the length and position of sequence with adenine homopolymers, as these features could be identifying for each fragment.

Figure 17:
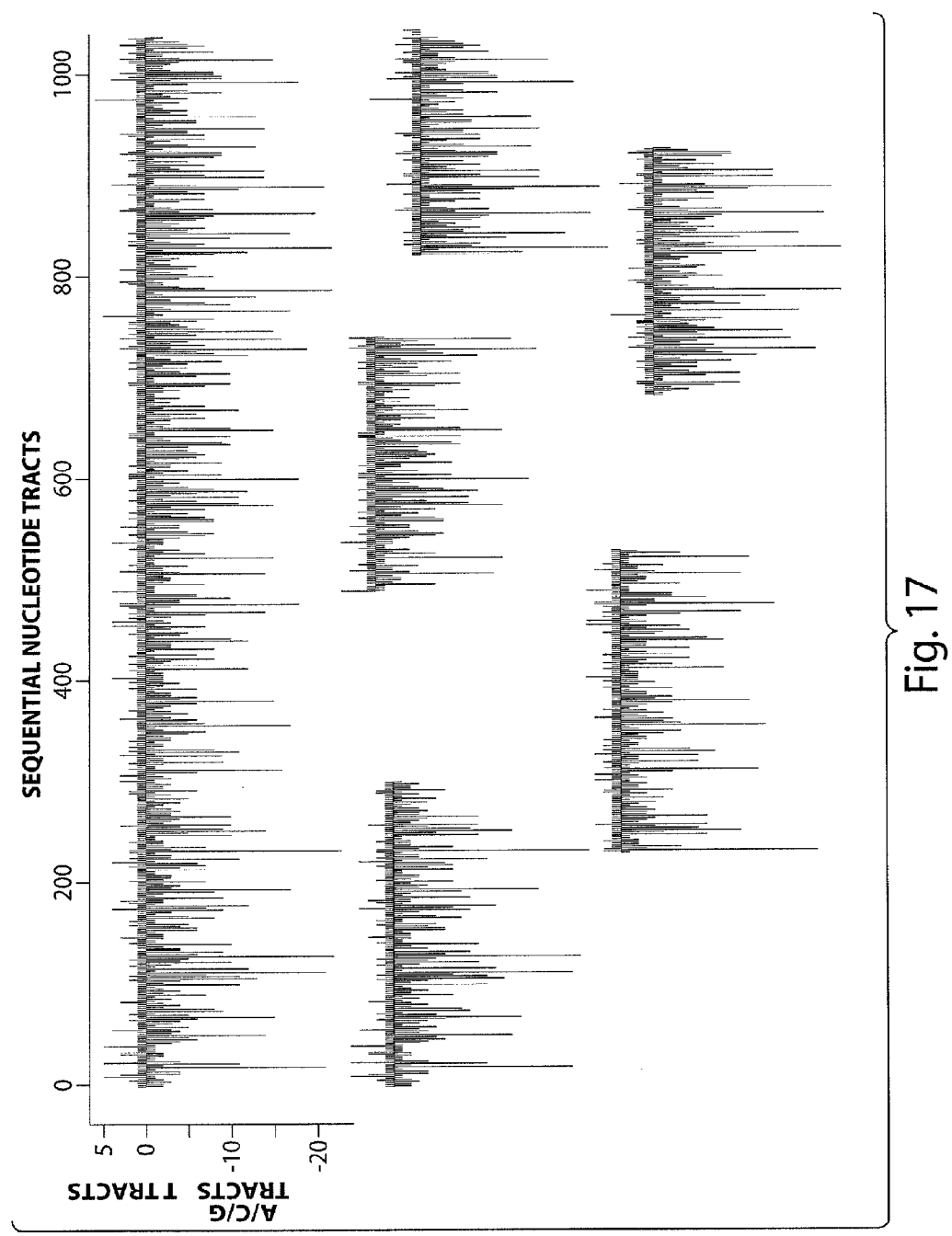
FIG. 17 is a set of sequence maps relating to the same nucleic acid region and generated using a three dNTP mixture and separate one dNTP flow regimen.

Once such a map is generated, it can be used as a scaffold for shorter, base-by-base reads permitting assembly and orientation of data from all reads. FIG. 17 is a schematic representation of contig assembly and orientation using data from such a sequencing reaction. The position and length of T nucleotide tracts relative to tracts comprised solely of A, C and G nucleotides permits five shorter reads to be effectively over-lapped and oriented against the larger genome.

A typical sequencing cycle for some aspects of the invention may include washing of the flow chamber (and wells) with wash buffer, measurement of the position of the observable moiety tethered to the end of the template nucleic acid, introduction of a first dNTP species (e.g., dATP) into the flow chamber in the presence of polymerase, measurement of the position of the observable moiety, flow through of apyrase optionally in wash buffer, flow through of wash buffer, introduction of a second dNTP species in the presence of polymerase, and so on. This process is continued until all 4 dNTP (i.e., dATP, dCTP, dGTP and dTTP) have been flowed through the chamber and allowed to incorporate into the newly synthesized strands. This 4-nucleotide cycle may be repeated any number of times including but not limited to 10, 25, 50, 100, 200, 300, 400, 500, 600, 700, 800, 900, 1000 or more times. The number of cycles will be governed by the length of the target being sequenced and the need to replenish reaction reagents, in particular the dNTP stocks and wash buffers. Thus, the length of sequence that may be determined using the methods of the invention may be at least 50 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, up to and including 1000 nucleotides, 1500 nucleotides, 2000 nucleotides or more nucleotides.

Suitable polymerases can be DNA polymerases, RNA polymerases, or subunits thereof, provided such subunits are capable of synthesizing a new nucleic acid strand based on the template and starting from the hybridized primer. An example of a suitable polymerase subunit is the exo-version of the Klenow fragment of *E. coli* DNA polymerase I which lacks 3' to 5' exonuclease activity. Other suitable polymerases include T4 exo-, Therminator, and Bst polymerases. The polymerase may be free in solution (and may be present in wash and/or dNTP solutions) or it may be fixed to the solid support, one or more walls of the flow cell, the template, or the primers.

Figure 8A:
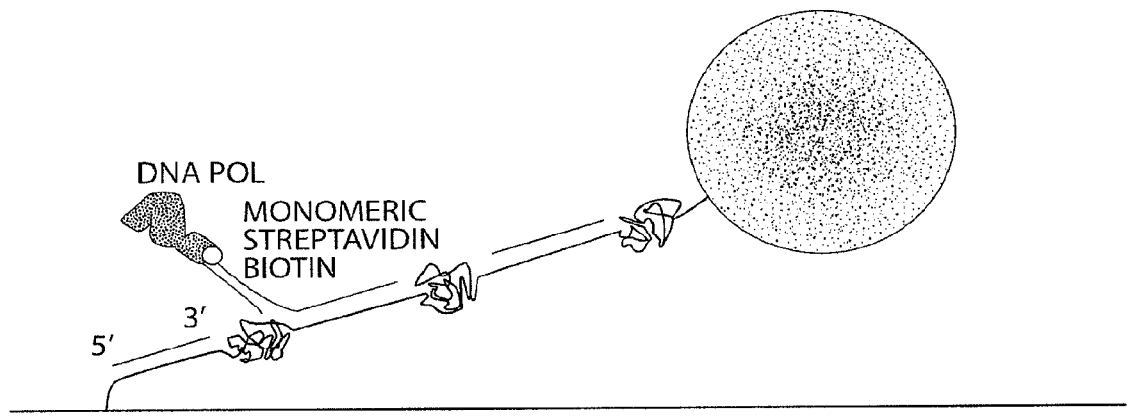
FIG. 8A illustrates a template tethered to a solid support and having a bead and a polymerase tethered thereto.

In some embodiments, the methods provided herein contemplate the use of a tethered polymerase, as shown in FIG. 8A. The polymerase may be tethered to the solid support or the template directly or indirectly (e.g., via a linker), and either covalently or non-covalently. Such tethering will increase enzyme processivity (i.e., the length of time the polymerase remains on the template and thus the number of nucleotides that are incorporated by the polymerase before it dissociates from the template). It will also reduce the amount of enzyme needed for the sequencing reaction since the enzyme will not be washed away with each flow through. Thus in one embodiment, the polymerase may be tethered (or attached) to the template or to primers hybridized to the template. Tethering to the template can be achieved through the use of a sliding clamp or a ring structure. In one embodiment, the polymerase acting on a primer is tethered to the 5' end of the primer immediately downstream. The polymerase may be tethered to the downstream primer using a double stranded oligonucleotide. Such an oligonucleotide may range in length in some embodiments from about 100-200 nucleotides. The oligonucleotide can be annealed to the template, of which only the most 3' 20 nucleotides are complementary (and act as primer). The exposed 5' tail is annealed to an oligonucleotide comprising a biotin at its 3' end, followed by the addition of a polymerase that is attached, covalently or non-covalently to streptavidin (preferably monomeric streptavidin) (Wu et al. *J. Biol. Chem.* 280(24):23225-23231 (2005); Howarth et al., Nature Methods 3:267 (2006)). Coupling of the polymerase to DNA can be achieved in other ways including, for example, using DNA modified with nitrilotriacetate (NTA) which has high affinity to a His-tag on a recombinant polymerase protein via the complexation of Ni(2+) (*Biotechnol Lett.* 30(11):2001-6 (2008)). Chemical coupling using engineered sulfhydryl groups or C-terminal thioester groups is another possible way to conjugate DNA to protein (Muir et al *PNAS* 95:6705-6710 (1998)).

Apyrase is an enzyme that degrades residual unincorporated nucleotides converting them into di- and ultimately mono-phosphates (and thereby rendering them unsuitable for DNA synthesis). It is therefore useful for degrading dNTPs that are not incorporated and/or that are in excess following a dNTP flow through. It is important that excess and/or unreacted dNTP be washed away before introduction of the subsequent dNTP in order to accurately determine the nucleotide that is incorporated and that is associated with the change in length of the template. Accordingly, addition of apyrase between the introduction of different dNTPs removes excess dNTPs that would otherwise confuse the sequencing data.

Additional amounts of sequencing reaction reagents such as those described above may be added throughout the reaction particularly if depletion of these reagents is expected, although in some cases this may not be necessary. For example, additional polymerase, DTT, SBB and the like may be added if necessary.

The sequencing reaction can be run at a range of temperatures. Typically, the reaction is run in the range of 30-60° C., 35-55° C., or 40-45° C. It may be preferable in some embodiments to run the reaction at temperatures that prevent formation of secondary structure in the template. However this temperature must also accommodate binding of the primer (and the newly synthesized strand) to the template and the reduced half-life of apyrase at higher temperatures. A suitable temperature is about 41° C. The solutions including the wash buffers and the dNTP solutions are generally warmed to these temperatures in order not to alter the temperature in the flow cell. The wash buffer containing apyrase however is preferably maintained at a lower temperature in order to extend its half-life. Typically, this solution is maintained at about 4-15° C., and more preferably at about 4-10° C.

The length of the oligonucleotide will be dictated by the length of the target. If a read-length of 1,000 bases is desired, the ssDNA region between two hybridized primers (essentially the length of the target) is at least about 1,000 nucleotides. Assuming a 3 pN flow, this number of nucleotides represents a length of about 50 nm in length, equivalent to about 150 base pair dsDNA. The activity of the tethered polymerase will remain on the primer upstream from that to which it is tethered because of the flow. An additional advantage of this configuration is that the distance to be covered by the tether becomes shorter as the polymerase synthesizes more and therefore the system actually improves at longer read lengths.

Other aspects of the invention are not sequencing-by-synthesis methods. In these aspects, sequencing may be carried out by hybridizing oligonucleotides (or probes) of known sequence to immobilized templates and detecting such hybridization by changes in the length of the template. The oligonucleotides may or may not have exogenous detectable labels on them, such as fluorophores or other optical labels. The invention is independent of the presence of such labels as the methods do not rely on detecting the hybridized oligonucleotides themselves but rather detecting the change in template length as a result of such hybridization.

This aspect of the invention contemplates obtaining sequence by flowing oligonucleotides over the immobilized template under conditions that allow the oligonucleotides to bind to the template if complementarity exists. Binding of the oligonucleotides results in conversion of single stranded bases into double stranded base pairs and therefore impacts the length of the template. The conditions may chosen to either maintain hybridization of the oligonucleotides throughout the sequencing reaction or to remove the oligonucleotides prior to flowing through subsequent oligonucleotides. The latter instance will likely increase the time to sequence and therefore the first instance may be preferable.

The oligonucleotides may be of any length including without limitation 2, 3, 4, 5, 6, 7, 8, 9, 10 or more nucleotides in length. They may be composed of natural or non-natural bases and backbones. Examples include peptide nucleic acids (PNA), locked nucleic acids (LNA), among others. The backbone may be comprised of phosphodiester linkages, and/or some modification thereof including but not limited to phosphorothioate linkages.

6. Other Applications

It will be understood that the sequencing methods provided herein have a number of applications including without limitation determining partial or complete nucleotide sequence of a nucleic acid (or a collection of nucleic acids such as exist in a genome, including mammalian genomes and more particularly human genomes), determining the presence or absence of a nucleic acid in a sample (as can be useful in for example diagnostic and forensic methods), determining whether the nucleic acid comprises a mutation or variation in sequence (such as for example an allelic variation including a single nucleotide polymorphism), determining whether a known nucleic acid has undergone mutation resulting in the generation of a new species (such as may be the underlying cause of antibiotic resistant microorganisms), determining the presence of a genetically modified organism or genetically engineered nucleic acids, determining whether and what genetic differences exist between two samples (such as for example normal tissue and diseased tissue), determining what therapeutic regimen will be most effective to treat a subject having a particular condition as can be determined by the subject's genetic make-up, and genotyping (e.g., analyzing one or more genetic loci to determine for example carrier status). In some of these embodiments, the nucleotide sequence determined using the methods of the invention may be compared to a known or reference sequence in order to orient the obtained sequence and/or to identify differences between the two. This may help to identify genetic variation and mutation. The known or reference sequence may be a previously determined sequence (for example, resulting from the complete genomic sequencing of a species).

The methods described herein can also be used to aid in the identification and treatment of condition. For example, the methods can be used for identifying a sequence associated with a particular condition or for identifying a sequence that is used to diagnose the absence of a particular condition. The samples being analyzed may be from any subject including humans. The condition may be cancer, a non-cancerous neurodegenerative condition, or an infection.

The methods can also be used to identify a sequence associated with a positive response to an agent. The method may comprise sequencing DNA from a plurality of subjects that exhibited a positive response and from a plurality of subjects that exhibited a negative response to an agent using one or more sequencing methods provided herein, and identifying a common sequence in the plurality of subjects that exhibited a positive response or from the subjects that exhibited a negative response that this sequence is not present in the other plurality of subjects. Preferably, the subject is a mammal, and more preferably a human.

The methods described herein may be automated such that the sequencing reactions are performed via robotics. In addition, the sequencing data obtained from a detector or a sensor may be input to a personal computer, a personal digital assistant, a cellular phone, a video game system, or a television, so that a user can monitor the progress of the sequencing reactions remotely.

The invention further contemplates kits comprising the various reagents necessary to perform the amplification and/or sequencing reactions and instructions of use according to the methods set forth herein.

One kit comprises one or more containers housing wash buffer, one or more containers each containing one of the following reagents: dATP buffer, dCTP buffer, dGTP buffer or dTTP buffer, dATP, dCTP, dGTP and dTTP stocks, apyrase, SSB, and polymerase. Importantly the kits comprise only naturally occurring dNTPs. The kit may additionally contain a contact sensor such as but not limited to a CMOS contact imager.

7. Resolution

The methods provided herein are dependent upon detecting incorporation of single nucleotides at each copy of a target in the template. As discussed herein, it is the relative movement of the observable moiety following flow through of single or combined nucleotides that indicates nucleotide incorporation. The limit of resolution is dependent upon the resolution of the detection system used.

Single base resolutions (i.e., distances or changes in distance on the order of $3.7 \pm 0.6$ Å) have been reported with extensive laser instruments (Abbondanzieri et al. *Nature* 438, 460-5 (2005)). However since the associated system throughput is tightly constrained by the resolution required for such analysis (van Oijen et al. *Biopolymers* 85, 144-53 (2007)), the statistical power of these results is limited.

Figure 10:
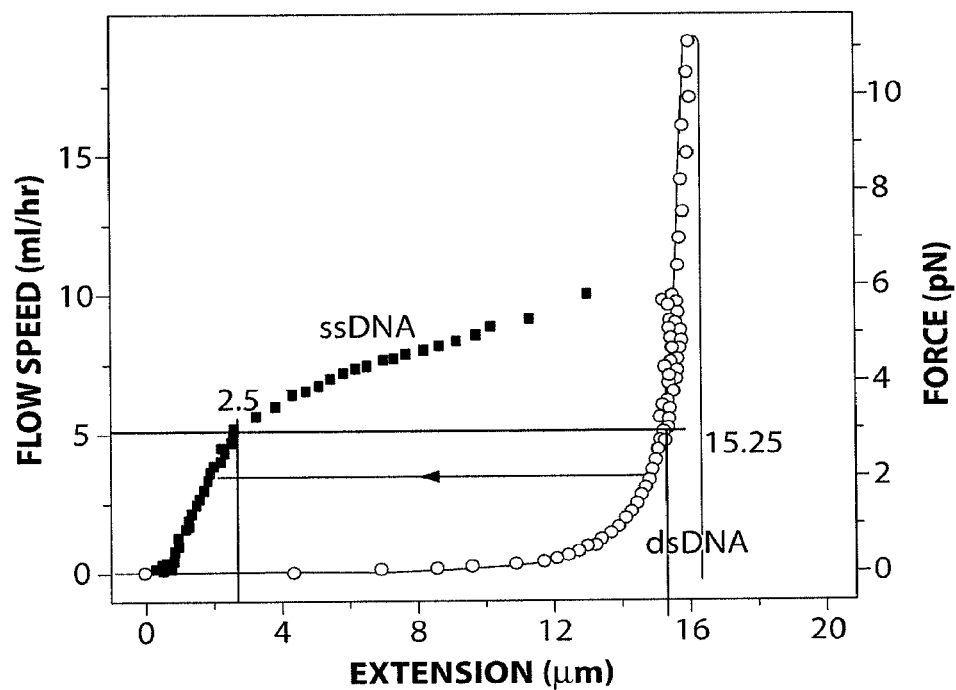
FIG. 10 is a graphical representation of extension of λ-phage ssDNA (open circles) and dsDNA (filled circles) both conjugated to a 2 μm bead, as a function of flow rate. The right vertical axis indicates the corresponding stretching force in pN. The change in DNA length that is caused by conversion of dsDNA to ssDNA at a force of 3 pN is indicated by the dashed or red line. This Figure is adapted from van Oijen et al. (*Science* 301, 1235-8 (2003)).

Flow stretching techniques, by comparison, utilize simpler, less expensive instrumentation (Smith et al. *Science* 258, 1122-6 (1992)), and employ lower-resolution wide-field microscopy which permits observation of many tethered templates simultaneously across an approximately 1 mm$^2$ field of view (van Oijen et al. *Science* 301, 1235-8 (2003)). While this large field of view permits observation of statistically relevant numbers of templates, the resolution is substantially worse, with a lower limit of 10 nm (i.e., 100 Å) at a bandwidth of 2 Hz (Kim et al. *Nat Meth* 4, 397-399 (2007)). FIG. 10 can be used to calculate the difference in relative lengths between ssDNA and dsDNA λ-phage DNA at 3 pN force. Based on calculations, this difference is approximately 12.75 μm (i.e., the difference between 15.25 μm (the length of dsDNA λ-phage at 3 pN) and 2.5 μm (the length of ssDNA λ-phage at 3 pN). When divided by the 48,502 base length of the DNA template, this converts to roughly 2.6 Å per base, so a 100 Å optical resolution equates to approximately 38 base pair resolution. In other words, conversion of 38 nucleotides from a single stranded to a double stranded form increases the length of a nucleic acid by about 100 Å. These calculations suggest that incorporation of a single dNTP onto the newly synthesized strands can be detected provided there are at least 38 (and preferably more) copies of the target in the template. That is, the signal from a single nucleotide incorporation must be amplified by at least 38-fold in order to be detected. It should be understood that the changes in template length are relatively independent of template length. In other words, if the force applied to the template is on the order of about 3 pN, then conversion of single stranded base to a base pair will increase length of the template by 2.6 Å regardless of whether the template is 1000 nucleotides in length or a $10^6$ nucleotides in length. The invention however contemplates that each template can be internally calibrated to determine absolute change in length as a result of single (or multiple) nucleotide incorporations using the key (known) sequences that are first sequenced. In this way, the extent to which the template will extend per nucleotide incorporation can be determined and used to analyze each template individually.

The templates typically will contain $10^3$ or more copies of the original circularized target nucleic acid. Each of the copies possesses an identical primer site, and each copy serves as a site for polymerase-based nucleotide incorporation and nucleic acid extension. As a result, the replicated copies on a single template undergo simultaneous and synchronous conversion from a single-stranded region to a double-stranded region at their 3' ends as each of the newly synthesized strands extends, thereby increasing the length of the template under flow. Thus, rather than incorporating a single nucleotide, the process incorporates simultaneously and synchronously a plurality of nucleotides. The number incorporated will depend on the target sequence (e.g., the presence or absence of a homopolymer stretch), the number of target copies in the template, the efficiency of binding of the primer, and the efficiency of polymerase extension at each site.

While lateral (i.e., x or y direction, which is in the plane perpendicular to the optical axis) optical measurement are possible for resolution on the order of tens of bases, on hundreds or thousands of beads simultaneously, z-axis measurements may allow simultaneous measurements and offer improved performance while retaining all of the benefits of wide field view optical microscopy. In addition, a higher density packing of tethered beads can be achieved since additional x by y area is not needed for elongation. Alternative tensioning forces could be applied, such as magnetic forces, while utilizing x or y direction flow merely for reagent delivery. In these instances, the invention contemplates that the template can be measured (i.e., the bead position can be determined) in the absence of flow. A stretching force parallel to the optical axis may be exerted by a magnetic, allowing templates to be stretched in a vertical direction, perpendicular to the solid substrate to which they are anchored. White light interferometric measurements can detect z-axis distance changes with approximately 1 Å resolution (Kim et al. *Nat Meth* 4, 397-399 (2007)), which is below the intrinsic Brownian motion distances.

It should also be noted that the accuracy of the flow stretching method of the invention will depend on Brownian motion, the random movement of particles through a liquid or gas. The amplitude of these random movements by a tethered particle is dependent on the force exerted on the tether. As an example, for the 48,502 base λ-phage DNA experiencing forces on the order of 2 pN, this equates to roughly 10 nm (van Oijen et al. *Science* 301, 1235-8 (2003)). However, averaging these movements over one second will decrease this value to approximately 5 nm. Additional averaging will improve this limit by a factor equal to the square root of the increase in acquisition time.

Figure 11A:
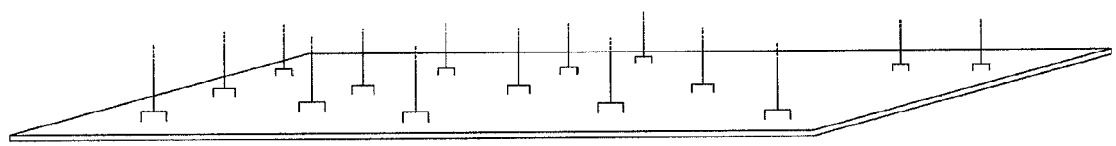
FIGS. 11A-F are diagrammatic representations of the sequencing-by-synthesis methodology of the invention employing the RCA-based template preparation, template tethering, and sequencing under flow induced tension.
Figure 11B:
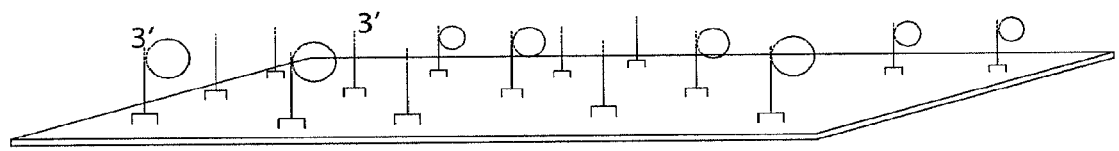
Figure 11C:
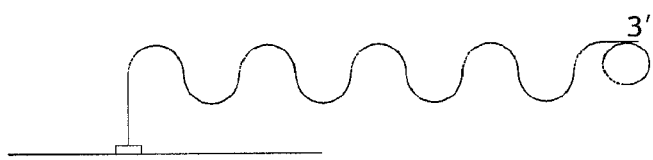
Figure 11D:
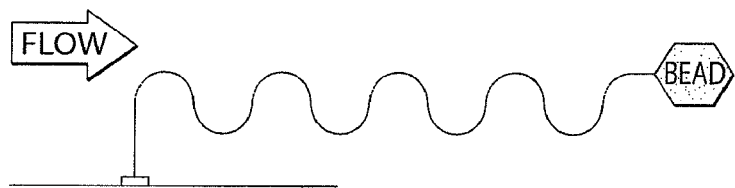
Figure 11E:
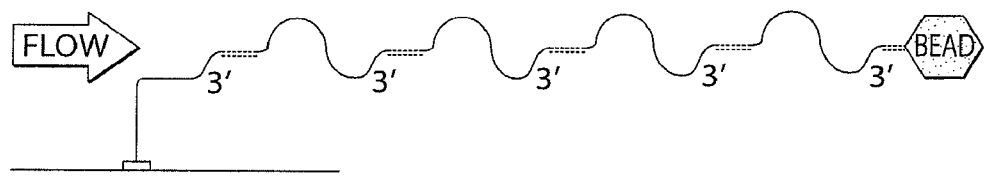
Figure 11F:
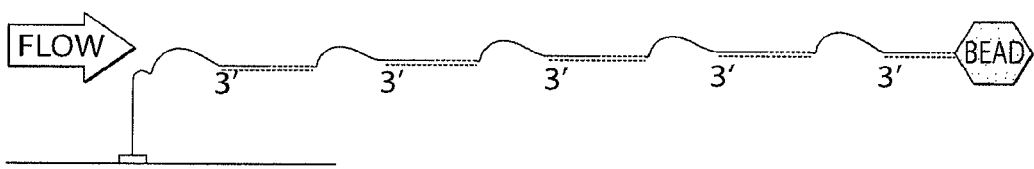

FIGS. 11A-F illustrate the RCA-based preparation of the template, tethering of the template to the solid surface and tethering of a bead to a template, and sequencing of the template under flow-based tension. FIG. 11A illustrates oligonucleotide primers that are immobilized to the surface of a slide through any of the existing biological or chemical attachment processes described herein. FIG. 11B illustrates circularized nucleic acids that possess a primer site and a target nucleic acid and that are hybridized to the immobilized primers via the complementary sequence on the 3' end of the immobilized primer. FIG. 11C illustrates the generation of the template as a result of extending the immobilized primer. FIG. 11D illustrates the direction of flow, as is contemplated in one embodiment, relative to the position of the bead-conjugated template. FIG. 11E illustrates primers hybridized to the plurality of primer sites on the template, thereby forming short double-stranded regions of DNA along the template. This serves to lengthen the template length under hydrodynamic flow as indicated by the movement of the bead to the right. FIG. 11F illustrates extension of primers hybridized to the template and its effect on the length of the template under flow, again as indicated by movement of the bead to the right. Addition of polymerase and nucleotides complementary to the next available position in the template results in polymerase-mediated primer extension at all priming sites on a template, generating additional double-stranded DNA regions and extending the length of the template under flow forces less than 6 pN by a proportional amount. This length increase during any specific nucleotide flow is detected and measured as described herein.

The importance of using concatamerized templates such as those generated by RCA is illustrated by the following calculation. By replicating the target a thousand fold, the change in template length associated with sequencing one base at each of the thousand copies is effectively amplified from 2.6 Å (i.e., the difference in length achieved by converting a single stranded base into a double stranded base pair, as discussed above based on FIG. 10) to 2600 Å or 260 nm (i.e., the difference in length achieved by converting 1000 single stranded based into 1000 double stranded base pairs). Although RCA can amplify starting nucleic acids more than 1000-fold, the minimum resolution for single base incorporation on flow systems can be obtained with less than a 50-fold amplification, as discussed herein for simple optical detection systems. As a further example, for an approximately 50 kb template and a resolution of 10 nm (as can be achieved using simple optical detection systems), read lengths in excess of 1 kb are theoretically possible, as shown in Table 2. Subsequent improvements in resolutions can be easily converted into increased sequence read length per template without the need for greater amplification.

TABLE 2

Relationship between minimum resolution and maximum read length.

| Minimum resolution (Å) | Amplification required for single base resolution (fold) | Total DNA length (bp) | Maximum sequence length (bp) |
|---|---|---|---|
| 1000 | 382 | | 127 |
| 500 | 191 | | 254 |
| 250 | 95 | | 508 |
| 100 | 38 | 48502 | 1270 |
| 75 | 29 | | 1694 |
| 50 | 19 | | 2542 |
| 25 | 10 | | 5083 |
| 10 | 4 | | 12708 |
| 5 | 2 | | 25415 |

Grey row indicates reported flow-based DNA tensioning data as derived from van Oijen et al. *Science* 301, 1235-8 (2003).

The methods of the invention also facilitate sequencing of homopolymer regions in the template. As used herein, homopolymer regions are regions within the template that consist of two or more contiguous identical nucleotides (e.g., $A_n$, $T_n$, $C_n$, or $G_n$, wherein n is 2 or more). These regions are difficult to sequence using some prior art approaches because it can be difficult to discern between incorporation of one, two, three, four, or more nucleotides of the same type. This situation does not present an issue for the instant methods because the extension of the template per nucleotide incorporation occurs independently of every other nucleotide incorporation. Instead, the effective change in template length scales linearly with homopolymer length. For example, assuming a template having 1000 concatamerized copies of a target under a 3 pN tension (see FIG. 10), a homopolymer that is 2 nucleotides in length will effectively result in 2000 nucleotide incorporations which will increase the template length about 5200 Å (or 520 nm), while a homopolymer that is 10 nucleotides in length will effectively result in 10000 nucleotide incorporations which will increase the template length about 26000 Å (or 2.6 µm). The absolute movement of the observable moiety (e.g., the bead) increases as the homopolymer region increases in length, while the absolute error on such measurements changes remains unchanged. The resultant increase in "signal-to-noise" (i.e., the measured length to error ratio) provides the possibility of greater accuracy with increased homopolymer size, precisely the type of sequence motif that challenges current next-generation sequencing systems (Margulies et al. Nature 437, 376-80 (2005)).

8. Imaging/Detection System

The invention contemplates any variety of imaging devices and systems capable of detecting the observable moiety at the end of the template. The imaging device or system should be sufficiently stable to visualize the changes in length of the template.

One imaging system contemplated by the invention is a computer controlled charged coupled device (CCD) camera attached to a microscope situated above the solid support, as shown in FIG. 2. The flow-based stretching methods provided by the invention have the advantage of allowing a large number of events to be observed per run (van Oijen et al. *Biopolymers* 85, 144-53 (2007)) through the use of low resolution microscopy to produce the greatest field of view. These configurations observe about 450-500 molecules (van Oijen et al. *Science* 301, 1235-8 (2003)) per run.

Figure 12A:
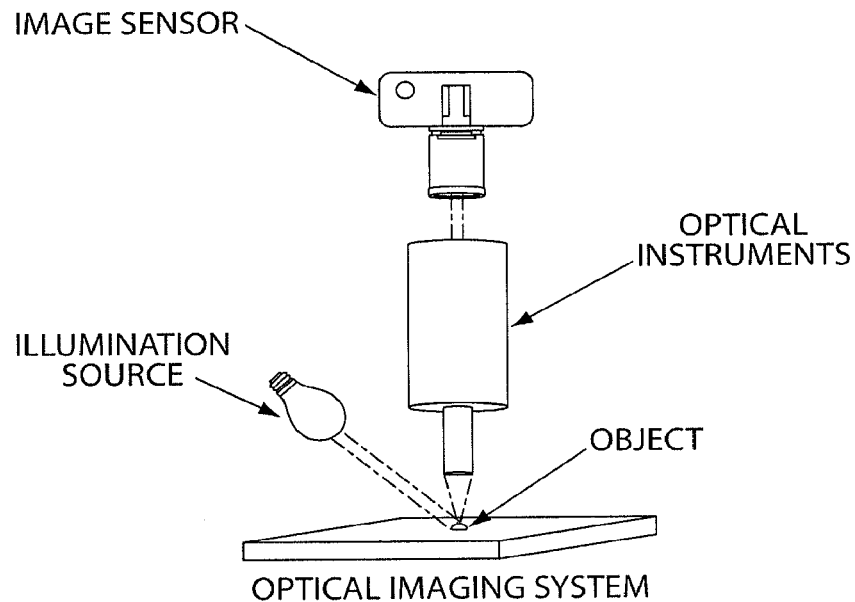
FIGS. 12A-B illustrate a conventional optic imaging system that consists of a microscope and camera (A) and a contact imaging system in which the object is placed directly on the sensor surface (B). The Figure is taken from Ji et al. (*IEEE Transactions On Circuits And Systems Part 1 Regular Papers* 54, 1698 (2007)).
Figure 12B:
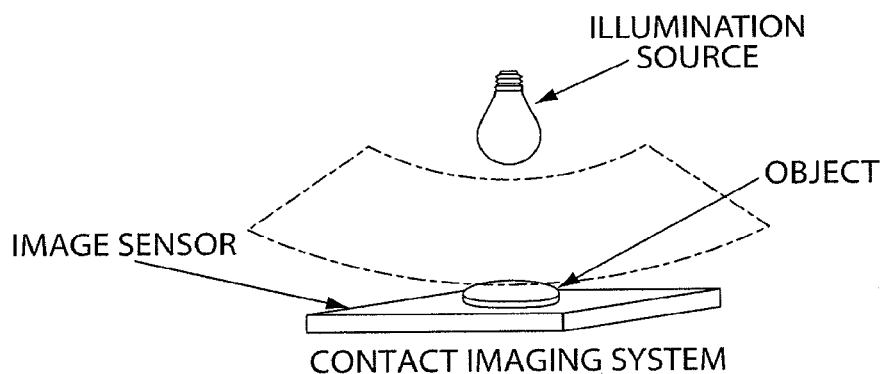

Another imaging system contemplated by the invention employs low-cost, commercially available contact image sensors, embodiments of which are illustrated in FIGS. 12A and B. Contact image sensors comprise an image sensor that is placed in very close proximity to the object to be imaged. An illumination source (typically but not necessarily from an LED) projects a shadow from the object directly onto a linear array of detectors (in this case the pixels of a CMOS chip), as opposed to imaging systems that require optical lenses and/or mirrors to transmit light to a distant camera as shown in FIG. 12A.

Figure 13:
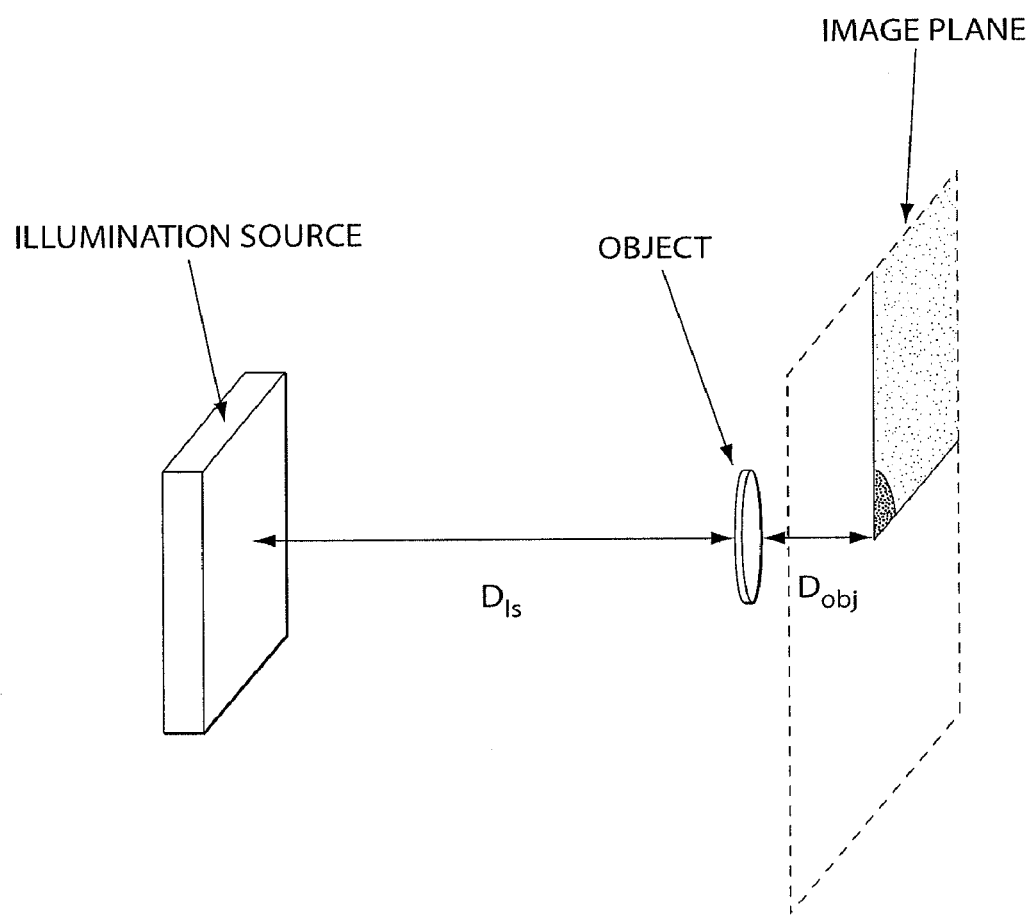
FIG. 13 illustrates a simulated model of a contact imaging system.

Certain currently available CMOS systems are comprised of detector pixels smaller than the 2.8 micron diameter bead (contemplated by one embodiment of the invention) and its projected shadow. (See for example Micron Technology which offers 5 and 9 megapixel CMOS imagers with 1.75 and 2.25 micron pixels respectively.) As a result, the location of the projected shadow of the bead on the surface of the detector can be accurately determined as shown in FIG. 13. Use of LEDs as the light source allows these sensors to be highly power efficient, and the modular nature of the detector allows them be smaller, lighter and less expensive than CCD systems. As the maximum depth of field for the sequencing reactions of the invention is limited by the height of the flow cell, the contact imager's limited focal plane is not detrimental, and has been shown to be effective for a variety of biological applications including cell imaging (Ji et al. *Circuits and Systems*, 2006. ISCAS 2006. Proceedings. 2006 IEEE International Symposium on, 4 (2006)).

Figure 14:
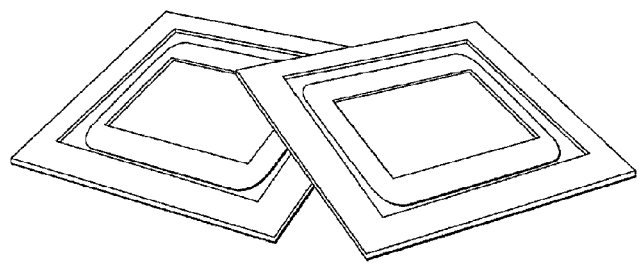
FIG. 14 provides an example of a CMOS image sensor.
Figure 15:
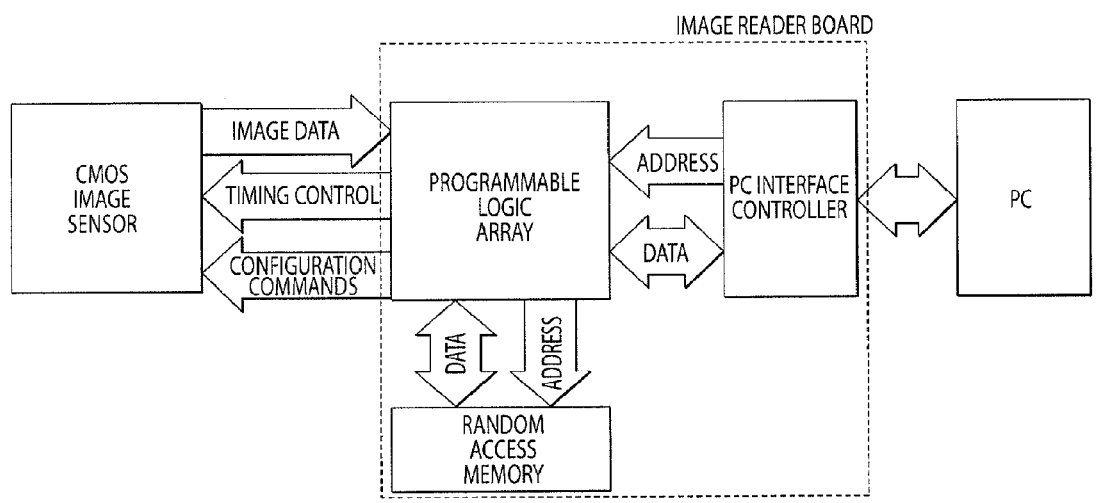
FIG. 15 is an exemplary CMOS image reader board block diagram.

Thus, in some aspects, imaging of the observable moiety (e.g., the 2.8 µm bead) may occur using a CMOS image sensor, modified to allow direct placement of the items to be imaged on the imager surface, with a supporting fluidic cell. CMOS image sensors may encapsulate light sensing, analog-to-digital conversion, and associated support circuitry, on the same integrated circuit die (chip). An example of such a CMOS sensor is shown in FIG. 14. Supporting hardware will have functionality as depicted in FIG. 15. The reader board will provide required timing signal communications with the CMOS sensor, provide configuration commands to the CMOS sensor, and receive digital image data acquired and digitized by the CMOS sensor. The reader board will use programmable logic (e.g., an FPGA(s)) as the stable timing and command interface source. Image buffering will be via connected random access memory (RAM). The reader board will be able to communicate with a PC over a standard bus (e.g., USB) and may employ an interface controller (e.g., USB controller) for this purpose.

Figure 16:
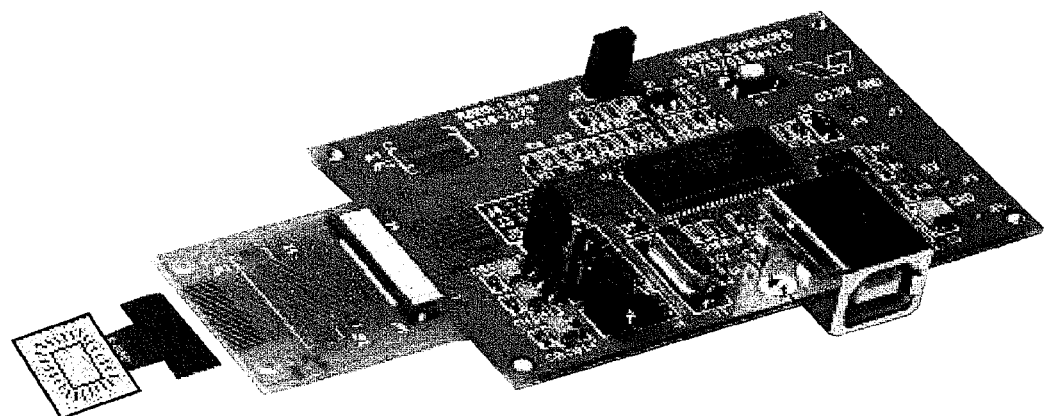
FIG. 16 is an example of a CMOS image reader board.

The CMOS image reader board will provide the above functionality in the form of a standard printed circuit board such as depicted in FIG. 16. The connection to the CMOS sensor will be designed for repeated connection and disconnection of a CMOS image sensor, to facilitate frequent replacement of the CMOS image sensor. Examples of such a connection are a ribbon cable with releasable connector, a ZIF socket, standard connector, or integrated circuit (IC) socket, but are not so limited.

It is to be fully appreciated that successful addition of a CMOS chip to the platform would also enable applications that utilize signals generated by any of the photon generating processes known in the field such as fluorescence, luminescence (both biological and chemical), and the like to track bead location and movement.

Additionally, techniques wherein the template itself is visualized, either through DNA-specific stains or incorporation or hybridization of either fluorescent or light generating moieties (e.g., fluorescently labeled nucleotides or probes) could be used to measure the actual length of the template under tension rather than the position of the bead.

The invention contemplates still other detection schemes for measuring movement of the observable moiety, particularly when the moiety is a bead. Thus, in another embodiment, the invention contemplates measuring bead movement through an electrical measurement of impedance (see Gawad et al. *Lab Chip* 1, 76-82 (2001); Fuller et al. *Micro Total Analysis Systems* 2000: Proceedings of the [Mu] Tas 2000 Symposium, Held in Enschede, the Netherlands, 14-18 May 2000 (2000); Sohn et al. *PNAS* 97, 10687 (2000)). Such measurements have been demonstrated using 3 µm polystyrene beads (Medoro et al. *Sensors Journal, IEEE* 3, 317-325 (2003)).

9. Detection, Measurement and Sequencing Software

Figure 18:
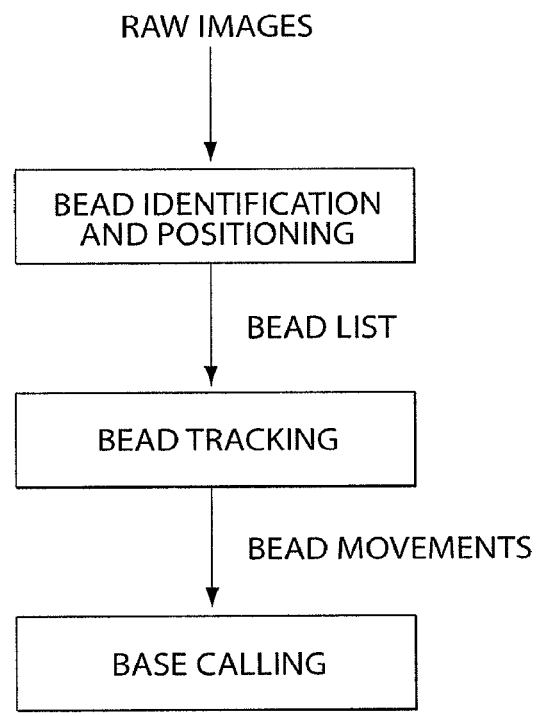
FIG. 18 is an algorithm for bead identification, tracking and ultimately base calling.

The systems provided herein involve tracking and measuring movement of observable moieties attached to templates such as beads. This includes identification of the moiety, calculation of its position (preferably with nanometer accuracy), and tracking changes in its position over many nucleotide flows (FIG. 18). For each flow, the set of tracked moieties is then updated, and normalized movement information is output for each moiety. These normalized movement data are interpreted by a base caller algorithm executed on a computer such as a personal computer, a work station, a networked computer, a distributed computing system, and the like, as will be appreciated by those of ordinary skill in the art, and sequence data are output (e.g., to a file on a storage medium such as a hard drive, on a screen display, both, or to other output devices, such as to a network interface for transmission to another computer or data store). Specific software tools are employed in each of these phases, as described herein.

For convenience, the following example assumes the moiety is a bead. Initially, a raw image is processed to identify a set of beads contained within the image, and to determine, for each bead, a sub-pixel position within the image. Beads can be found by, for example, identifying local minima within the image. Bead positions can be found using any suitable technique such as, for example, by calculating a moment, and further refining that position with multiple Gaussian fits over the bead pixels. The output Gaussian fit parameters can be used to further remove poor fits, which are typically image artifacts or multiple touching beads.

Bead position accuracy is important for achieving high system throughput and for maximizing bead loading density. From simulations of 12-bit gray-scale images with typical noise levels, it was found that a bead ideally should occupy about 1.6 pixels in the output image. Position accuracy may be obtained, for example, by calculation of the center of mass of the bead, essentially a 2D intensity-weighted moment calculation, such as described by Feng and coworkers (Feng et al. *Rev Sci Instruments* 78, 053704-10 (2007)). Also important is the determination of the set of pixels that influence the bead position (Feng et al. *Rev Sci Instruments* 78, 053704-10 (2007)). Improvements are provided over the published methods by introducing local background average baseline intensity calculations, thus improving the threshold determination for bead-containing pixels. The position of the bead may be further refined through the use of Gaussian curve fits to the beads, using the moment calculation position as an initial input. A similar method was shown by Yildiz et al. (*Science* 300, 2061-5 (2003)). Further improvements in the position can be achieved by averaging the calculated bead positions over multiple images, provided those images represent the beads in a stable condition, such as would be the case when any incorporation has been expected to go to completion for a given flow.

An exemplary algorithm is as follows:

1. Calculate a local reference image intensity by blurring the original image with a standard Gaussian blur function, with radius of 50 (or roughly 3% of the width of the image).

2. Examine image for local minimums by considering each pixel one at a time. A pixel is added as a potential bead if the value of that pixel is equal to or less than each of the eight surrounding pixels.

3. Perform a moment (center of mass) calculation on the pixel by first considering the 5 pixel×5 pixel area centered at the given pixel. Each pixel is compared to the local average intensity at that location, and pixels with a value less than the average background intensity value are summed, weighted by their intensity delta from that background. This step will yield a position within approximately 20 nm accuracy.

4. Perform a Gaussian fit in both the horizontal and vertical directions, using the previously calculated bead position as an initial input to the fit. A simple levmar (Levenberg-Marquardt) iterative approach yields a fast and accurate refined bead position.

5. Account for mechanical drift by subtracting out position changes as detected by immobilized beads or other immobilized reference markers.

6. Perform an average of the calculated bead position for each bead over multiple images, at least two images minimum. The final set of bead positions is output for each nucleotide flow, for use in the tracking portion.

Given a set of beads in one time frame, and a (similar) set of beads in a later time frame, the goal is to track the beads between the two frames, and thus determine the distance each bead moves between frames. This process occurs for each frame in the run. Here, a frame represents the calculated bead position for each bead, after a nucleotide flow has occurred, and any incorporation events have occurred.

A typical example is shown in Table 3.

TABLE 3

| Item | value |
| --- | --- |
| CCD Pixel dim | 4096 |
| CCD pixel pitch (µm) | 1.75 |
| CCD pixels/bead | 1.6 |
| bead diameter (µm) | 2.8 |
| bead coverage (%) | 0.15 |
| pixel area (µm$^2$) | 51380224 |
| plate dimension (side) (µm) | 7168 |
| bead area (µm$^2$) | 7707034 |
| beads required | 1251645 |
| tracking percent | 0.635 |
| beads usable | 794795 |

Tracking is complicated by the fact that, on average, only about 56% of the beads move in any flow (assuming 2.25 incorporation events per 4 reagent flows). While small movements are the most common, as seen with a 1 nucleotide incorporation, it is important to account for the possible movements of up to an 8 nucleotide incorporation event (as may occur with a template homopolymer that is 8 nucleotides in length). Beads from one frame are linked to beads in the other frame by searching for the closest bead pair between frames, for each bead.

Figure 19:
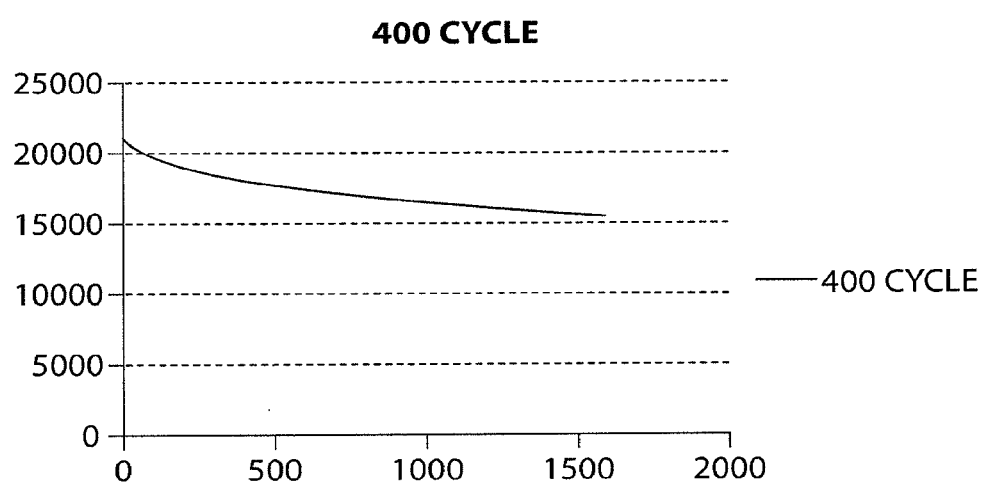
FIG. 19 illustrates a simulated model of the ability of bead tracking software to track beads over 1600 flows (i.e., 400 cycles assuming each dNTP is flowed separately).

A simulation modeling statistical bead movements over a 400 cycle run (i.e., 1600 individual nucleotide flows) demonstrated that it is reasonable to expect to accurately track 63.5% of the beads initially identified (FIG. 19). This assumes random initial placement, 15% loading density (by area relative to the slide), and 20 nm movement for a one-base incorporation.

The base caller algorithm takes the output from the tracking module and outputs sequence information per bead. The base caller preferably has knowledge of the order of nucleotide flow for a given run, and synchronizes that information with the tracking data per flow. Single template strands will typically exhibit distance movements that differ from bead to bead, with a normal distribution. For each individual bead, the engineered key sequence portion of the single molecule strand, which is first to sequence, is used to normalize each bead by establishing the length the bead will move for the various known extension lengths. Once normalized, the bead movement found at each flow can be used to determine the homopolymer length incorporated by a given nucleotide flow.

Various physical effects may reduce the clarity of the resulting signal measured (distance moved per flow in this case) over time. During the course of a typical run, it is possible that some primers may fall off, or fail to extend (signal droop), reagent activity may not completely extend in a timely manner on all sites (incomplete extension), or a previous reagent may not be completely washed out and could cause further incorporations during subsequent nucleotide flows (carry forward). The base caller algorithm preferably takes these effects into account, corrects for them, and is able to call bases for the long reads desired of the system.

The base caller algorithm takes the un-normalized signal-processed measurements output from the signal processing stage, along with the initial experiment data including reagent flow order, DNA template key sequence information, etc. The base caller algorithm converts this signal data into called bases. In order to produce high quality long reads, it may be necessary to do more than just linearly convert (by thresholding for example) the measured signal into a called base associated with each reagent flow. Many factors affect the signal measured, and the ability to produce an accurate long read is dependent on the software's ability to correctly de-convolve the signal and pull out the true incorporation signal. In summary, a base caller algorithm should correct for the effects of signal droop, background noise, carry forward effects, and incomplete extension effects.

Figure 21A:
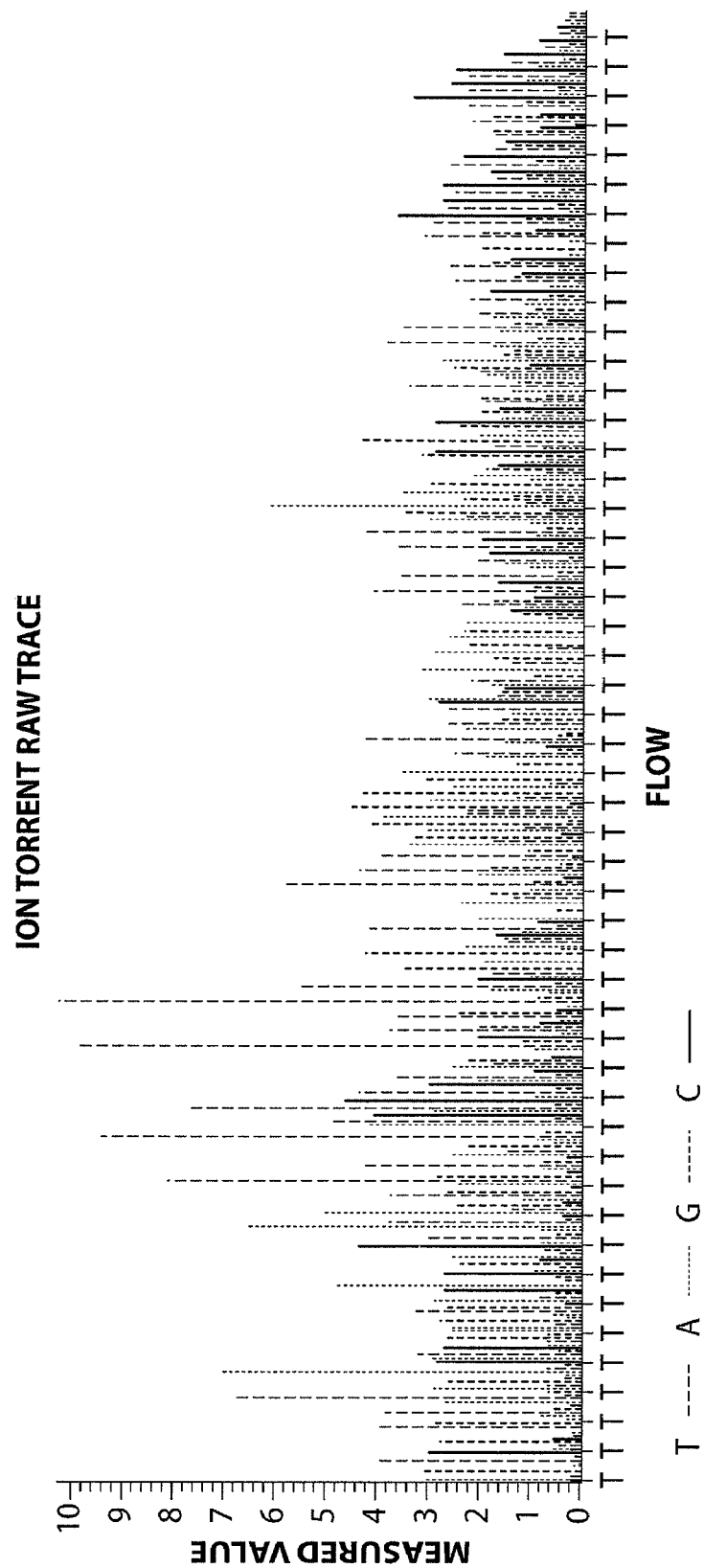
FIGS. 21A-B show base caller algorithm output for uncorrected (A) and corrected (B) data.
Figure 21B:
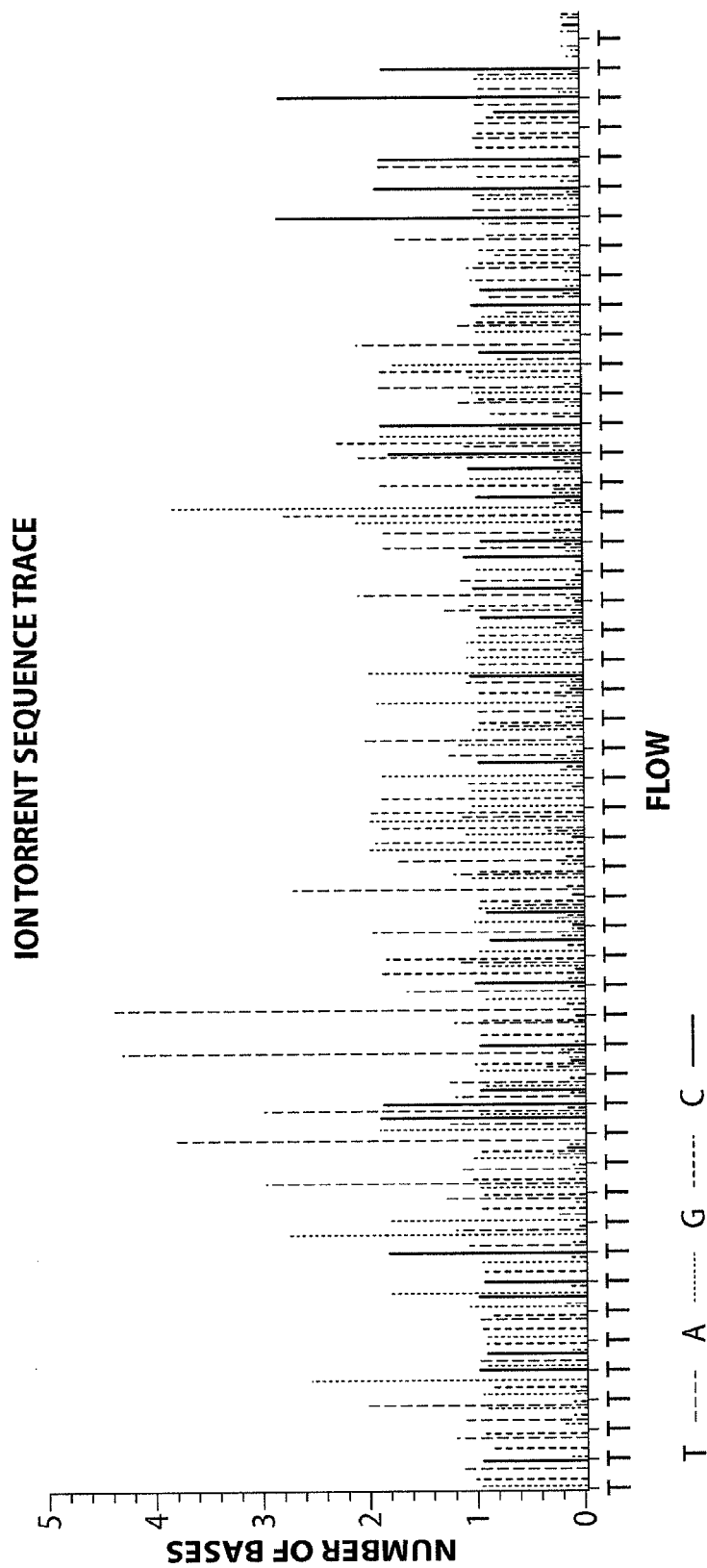

FIGS. 21A and B show base caller algorithm output for uncorrected (A) and corrected (B) data. The un-corrected flow trace quickly becomes difficult to interpret by eye. In the corrected flow trace, the read sequence is readily apparent. Essentially, over time, the signal degrades and experiences template phase shifts. For a given incorporation event, the signal is the sum of the signal generated by all of the DNA copies that extend in each sensor. Initially all copies are in phase, but with each reagent flow, some fraction fail to incorporate (incomplete extension), some fraction extends normally, and some fraction further extends due to previous reagents present (carry-forward). Normally, a state transition diagram depicting this type of model would grow $O(N)^3$, and traditional minimization approaches suffer from this exponentially complex problem.

The invention provides a predictive approach that leverages the fact that read-length is actually bounded, and thus there exists a finite number of states the DNA may be in prior to any nucleotide flow. So, rather than producing a $O(N)^3$ state transition graph, there is a linear $O(N)$ list that a computer simulation may easily deal with. Given this list of states for the template copies contained within the single molecule strand, a model that shifts percentages around among those states is built, and by applying the modeled states to a new nucleotide incorporation event, a prediction of the signal is made for each of a zero-mer incorporation through for example an eight-mer incorporation, and a best-fit for that event can be made from the measured signal, and the model updated with the new state information. This approach proves to be extremely fast.

The invention therefore provides in other aspects methods and algorithms, including software algorithms to be executed by a computer, that relate to detection of beads, measurement of bead movement, and sequencing of nucleic acids as a result thereof. Certain algorithms present improvements over prior art methods for detecting and monitoring moieties such as beads. These improvements include determining and using local background average baseline intensity, thereby improving the threshold determination for bead-containing pixels. In these algorithms, a local background is calculated and is subtracted from a test intensity value. Importantly, local backgrounds are used rather than average backgrounds that are calculated across the entire image. This approach allows data to be obtained even from low quality images.

Certain methods and algorithms involve the use of internal reference moieties (e.g., beads) that are designed not to move as a function of nucleotide incorporation. These reference moieties however may move for other reasons, and it is expected that moieties tethered to the template will move on average to the same degree. Such movement is referred to herein as "background movement". The invention contemplates subtracting such background movement from the measured movement of template-tethered moieties in order to more accurately identify movement that is the result of nucleotide incorporation rather than movement caused by other factors. Preferably, the reference moiety and the template-tethered moiety are of the same type or nature (e.g., both are beads).

The base caller algorithm in some instances is designed to take into consideration (or account for) various errors that can occur during the sequencing reactions. Examples include incomplete extension in which not all possible dNTPs are incorporated into one or more of the newly synthesized strands, carry-forward errors in which a fraction of unincorporated dNTPs remain in the flow cell and are thus available for incorporation in subsequent steps, and signal droop. A suitable algorithm can address one, some combination, or all of these and other quantifiable errors.

EXAMPLES

Example 1

Current XTM Sequencing Protocol

Example 1A

RCA Formation and Attachment to Slides for XTM Sequencing

Generation of Circles from oligos using CircLigase™ from Epicentre® (Follow Protocol with 5'P Oligo of 50-70 bp)

Ligate 100 pmols of oligo in 200 µL—60 mins at 60° C., 20 minutes 80° C. (100 µM ssDNA template: 1 µl (final 0.5 pmol/µl) Reaction conditions: 10× CircLigase™ Buffer: 20 µl, 1 mM ATP: 10 µl, 20 mM MnCl2: 10 µl, CircLigase™ (100 U/ul): 10 Water: 149 µl (TOTAL: 200 µl)

ExoI treat with 5 µL NEB ExoI directly in ligation reaction after heat kill step—37° C. for 45 min, 80° C. 20 minutes Run 15% Urea PAGE gel to determine yield and gel shift indicative of circularization—stain with SybrGold Typical yield is 0.2 pmol/µl Generation of Circles from Double Stranded DNA Fragments (PCR or Genomic Fragments)

Prepare 2 ug of (100 ul of 20 ng/ul) 5' biotinylated DNA fragments (200-600 bp) by either PCR with 5' biotin forward primer, or ligation of adaptors to each end with left adaptor having 5' biotin moiety. Add equal volume of 2× binding and wash buffer, (2M NaCl, 10 mM Tris HCl pH7.5, 1 mM EDTA) for a final volume of 200 uL.

Immobilize DNA fragments to 10 uL streptavidin coated beads (M280 streptavidin coated beads, Invitrogen) in 1× binding and wash buffer Wash beads twice in dH2O using magnet to separate beads. Melt DNA using alkaline wash (125 mM NaOH) and collect supernatant containing ssDNA. Apply ssDNA to Microcon 30 filter unit (Millipore), filter to dry, capturing the ssDNA on the filter surface and then resuspend in original volume with 10 mM Tris HCl pH 7.0, 1 mM EDTA.

Hybridize Guide oligo complementary to sequences at 5' and 3' end of DNA (adaptor sequence) such that 5' and 3' end of ssDNA is juxtapose (ref 54). Ligate to close circle with T4 DNA ligase. The Guide oligo can be functionalized at the 5' end for immobilization onto the surface of the slide (e.g. 5' biotin, 5'Amino, 5' Sulfhydryl, for example).

Prehybridization of Primer with Circle

Hybridize 4 pmol of circles to 0.4 pmol of 5' NHS or biotin labeled primer 9.5 μl each of A & T circle (approx. 0.2 pmol/1 each) 1 μl of 0.4 μM amino primer (TOTAL: 20 μl) 60° C. for 5 minutes, −0.1 C/s to 50° C. hold for 5 min, −0.1° C./s to 40° C. hold for 5 minutes, −0.1° C./s to 15° C., Hold at 15° C. For above 20 μl, add 2 μl of 10× printing buffer (500 mM Sodium Phosphate pH 8.5). For in tube RCA, use 5 μl of circle/primer mixture (i.e. 1 pmol of circle and 0.1 pmol of primer)

For above 5 add:
10× RepliPHI buffer: 2 μl
1 mM DTT: 0.8 μl
2 mM dNTP: 10 μl
10 mg/ml BSA: 0.4 μl
Phi 29 polymerase: 1.4 μl
G32: 0.2 μl
YIPP: 0.2 μl
(TOTAL: 20 μl)
30° C. 20-60 min
Heat denature 45° C. 15 min
Final concentration is 0.02 pmol/μl use 20 μl per slide Binding of Primer/Circles to Slides For NHS peg slides (Microsurfaces Inc.), rinse slides in 1×PBS+10% glycerol then rinse once with 1× printing buffer (50 mM Sodium Phosphate pH 8.5) and incubate 22 μl of 5' amino primer/circle hybridization solution (in printing buffer) under cover slip in water tight hyb chambers (Corning) for 30 minutes at room temp.

For Bio peg slides (Microsurfaces Inc.) pretreat slides with 20 μl of 20 μg/ml streptavidin in 1×PBS+10% glycerol in water tight hyb chambers (Corning) for 30 minutes at room temp. Wash slides in 1×PBS+0.05% Tween 20. Incubate 20 μl of 5' dual biotin labeled primer/circle hybridization solution under cover slip in water tight hyb chambers (Corning) for 30 minutes at room temp Wash slides bound with primer circles 3× in 1×PBS+ 0.05% Tween20. For NHS slides block unreacted NHS sites with deactivating agent (proprietary to Microsurfaces Inc., but 20 mM Ethanolamine or 50 mM Tris acceptable) by flooding slide with 500 μL for 1st wash, replace with another 500 μL for 15 min, and replace with another 500 μL for 15 min at room temperature.

Wash 3× in 1×PBS+0.05% Tween 20

RCA Reaction

On Slide

Use phi29 DNA polymerase from Epicentre® and kit reagents—20 μL per slide

Include G32 protein (1 μL per 100 μL reaction volume)
Include yeast inorganic pyrophosphatase (1 μl per 100 μL reaction volume)

Reaction conditions:
10× RepliPHI buffer: 2 μl
100 mM DTT: 0.8 μl
10 mM dNTP: 2 μl
10 mg/ml BSA: 0.4 μl
Water: 13 μl
Phi 29 polymerase: 1.4 μl
G32: 0.2 μl
YIPP: 0.2 μl
(TOTAL: 20 μl)

If in Need to Add Sequencing Primer, Prepare 4 μM and Add 1 μl in 20 μl Reaction (accordingly, water should be added as 12 μl)

Wash slides 1× with 1× phi29 buffer
Incubate RCA reaction under clover clip for 20-60 minutes at 30° C. Stop by floating cover slip in 1×PBS+50 mM EDTA and incubating at 45° C. for 15 minutes.

In Tube

The RCA reaction can be done in solution in a tube. The reaction conditions are the same as the conditions employed for the on slide RCA except no EDTA is used to stop the reaction. Primer/circle template is prepared as above. The reaction is stopped after incubation at 30° C. for 20-60 minutes by heating to 45° C. for 15 minutes.

Labeling RCA ssDNA with BstL Incorporation of Modified dUTP

On Slide

Following heat kill of phi29, wash slide in 1× Thermopol buffer

Add 20 ul BstL labeling reaction to slide and incubate at 45 C for 1 minute under coverslip.

Recipe:
Water 14 μl
10× Thermopol Buffer: 2 μl
10 mM each dNTP: 0.4 μl
1 mM dUTP with modification: 1.0 μl
Modified dUTP could include biotin-dUTP, aminoallyl-dUTP or Digoxigenin-dUTP
BstL DNA polymerase: 1.0 μl
(TOTAL: 20 μl)
Wash 3× in 1×PBS+0.05% Tween 20
Dip in 50 mM NaOH for 10 seconds to remove circles
Wash 3× in 1×PBS+0.05% Tween 20

In Tube

If the RCA reaction was done in tube, then following heat kill the 20 ul RCA has 20 ul of a 2× BstL labeling reaction added 2× BstL recipe
Water 11.2 μl
10× Thermopol Buffer: 4 μl
10 mM each dNTP: 0.8 μl
1 mM dUTP with modification: 2.0 μl
BstL DNA polymerase: 2.0 μl
(TOTAL: 20 μl)

Reaction tube incubated at 45° C. for 1 minute
The reaction is stopped by the addition of 5 μL 500 mM EDTA The reaction buffer is exchanged with printing buffer using an Microcon 30 filter device from Millipore, Billerica Mass. 300 μL of water is added to the Microcon 30 filter and the 40 μL RCA reaction is added. The device is spun at max speed on a bench top microfuge for 10 minutes (13000 rpm). Following the centrifugation step, the filtrate is discarded. 40 μL of 1× printing buffer is added to the membrane, and the RCA material withdrawn to a fresh tube.

The labeled RCA product can be bound directly to a PEG-biotin or PEG-NHS slide depending on the choice of 5' modification present on the RCA primer as described above for primer/circle preparations.

Primer can be annealed to RCA product in tube. See below.

Hybridize Sequencing Primer

On Slide

Add 1 pmol/μl sequencing primer in 1×PBS+0.05% Tween 20—20 μL per slide

Incubate under cover slip at 65° C. for 10 min, 50° C. for 10 min, and 30° C. for 10 min in hyb chamber Remove and cool to room temperature. Wash 3× in 1×PBS+0.05% Tween 20

Flood slide in 1× Thermopol buffer, Tap slide to remove buffer

Prepare 10 μL M280 beads (prewashed in 1× thermopol) in 50 μl 1× Thermopol.

Add 10 μL BstL (80U NEB).

Pipette 25 µL Bead/polymerase mix to center of slide. Allow to bind at room temperature for 15 min (for anti-DIG beads, a 2 hour incubation at room temperature is suggested). Load XTM flow cell.

For aminoallyl-end labeled DNA:

Prepare M270-Epoxy bead stock solution at 10⁹/ml in 100 mM sodium borate buffer (pH 9.0).

Take 10 µL of this stock solution and add 190 µL of sodium borate buffer and 100 µL of 3M ammonium sulfate (final 1M).

After primer annealing and wash with 1×PBS+0.05% Tween 20, pipette 25 bead/ammonium sulfate mix to center of slide.

Allow to hybridize at 37° C. overnight (16-24 hour) by gently agitating.

Wash with 3× 1×PBS+0.05% Tween20.

Flood slide in 1× Thermopol buffer, Tap slide to remove buffer.

Prepare 10 µL BstL in 300 uL 1× Thermopol

Pipette 25 µL polymerase/Thermopol mix to center of slide. Allow to bind at RT for 15 min. Load XTM flow cell.

In Tube

Add sequencing primer to a final concentration of 1 uM in 1× Printing Buffer.

Hybridize in thermocycler.

95° C. for 2 minutes
80° C. for 1 minute
−1° C./min to 40° C.
40° C. for 1 minute
4° C. hold Binding of RCA to Slides For NHS peg slides (Microsurfaces Inc.) wash slides in 1×PBS+10% glycerol then rinse once with 1× printing buffer (50 mM Sodium Phosphate pH 8.5). Wipe off the liquid leaving just the center of the slide wet (this is the place which flow cell will fit in later). Build the chamber by grease pen. Make sure there is no leak by pipetting in/out 100 µl of 1× printing buffer a few times.

Pipette 100 µl of RCA solution in the chamber and incubate 1 hr for dsDNA 40 min for ssDNA, RT. Place the slide in moist chamber supplemented with saturated NaCl solution.

Force/Extension and Polymerase Extension Data Obtained for RCA Tethered Bead

Figure 20A:
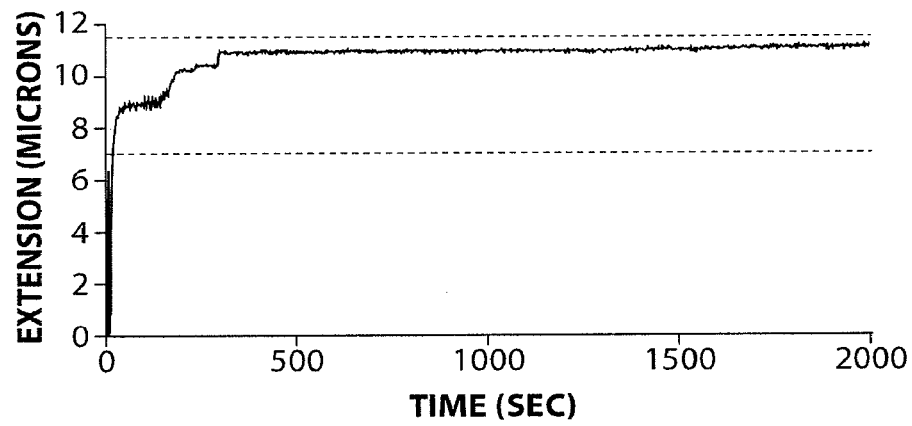
FIGS. 20A-C show extension versus time (A), force versus time (B) and force versus extension (C) of a single stranded DNA tethered to a bead as it undergoes polymerase-based extension to convert to double-stranded DNA.
Figure 20B:
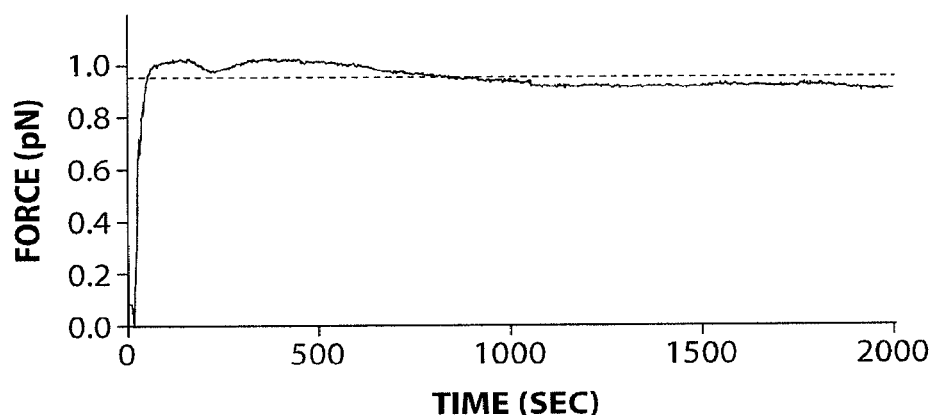
Figure 20C:
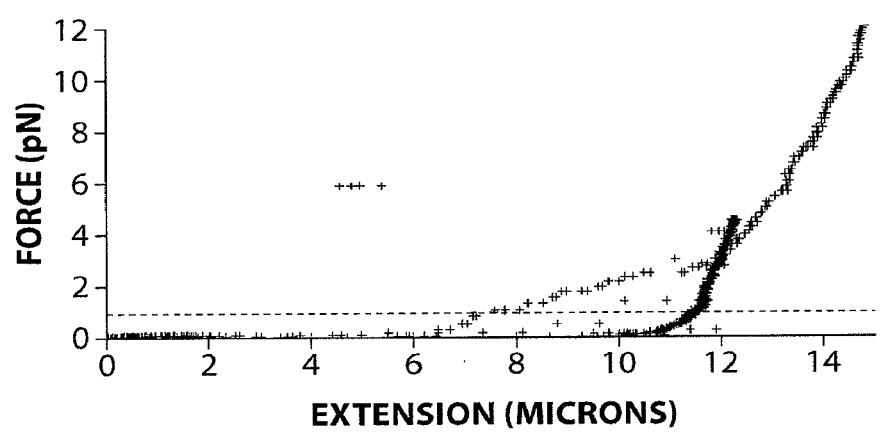

RCA product of 50 knt (50,000 nucleotides) approximate size with a 5' biotin terminal base, was generated from an 80 bp circle template and tethered to a PEG coated slide with low density biotin streptavidin couplings (Microsurfaces, Inc., Wis.). A 25 bp primer complementary to the RCA ssDNA was flowed in at 2 pN force for 5 minutes followed by a 15 minute incubation period with no force applied. After primer annealing, the tethered beads were subjected to slowly increasing force under flow, ranging from 0 pN to 12 pN then back to 0 pN. The extension of the DNA was measured by image capture. T4 exo minus DNA polymerase 100 nM was flowed in with 200 µM or dTTP, dCTP, dATP and dGTP at 1 pN force. Images were captured for 30 minutes. Following the DNA polymerase reaction, the slides were again subjected to force extension with buffer only ranging from 0 pN to 12 pN then back to 0 pN. Images were captured as before. FIG. 20A shows the extension of the bead during nucleotide incorporation when flow was fixed a 1 pN. FIG. 20B shows the flow force with time during nucleotide incorporation. FIG. 20C shows the stretching length and position of the bead before and after polymerase extension with increasing force. The initial force extension curves show the expected continuous extension up to 12 pN characteristic of ssDNA. The post polymerase force extension curves show the rapid increased length at low force followed by a decrease in further extension characteristic of dsDNA.

Figure 22:
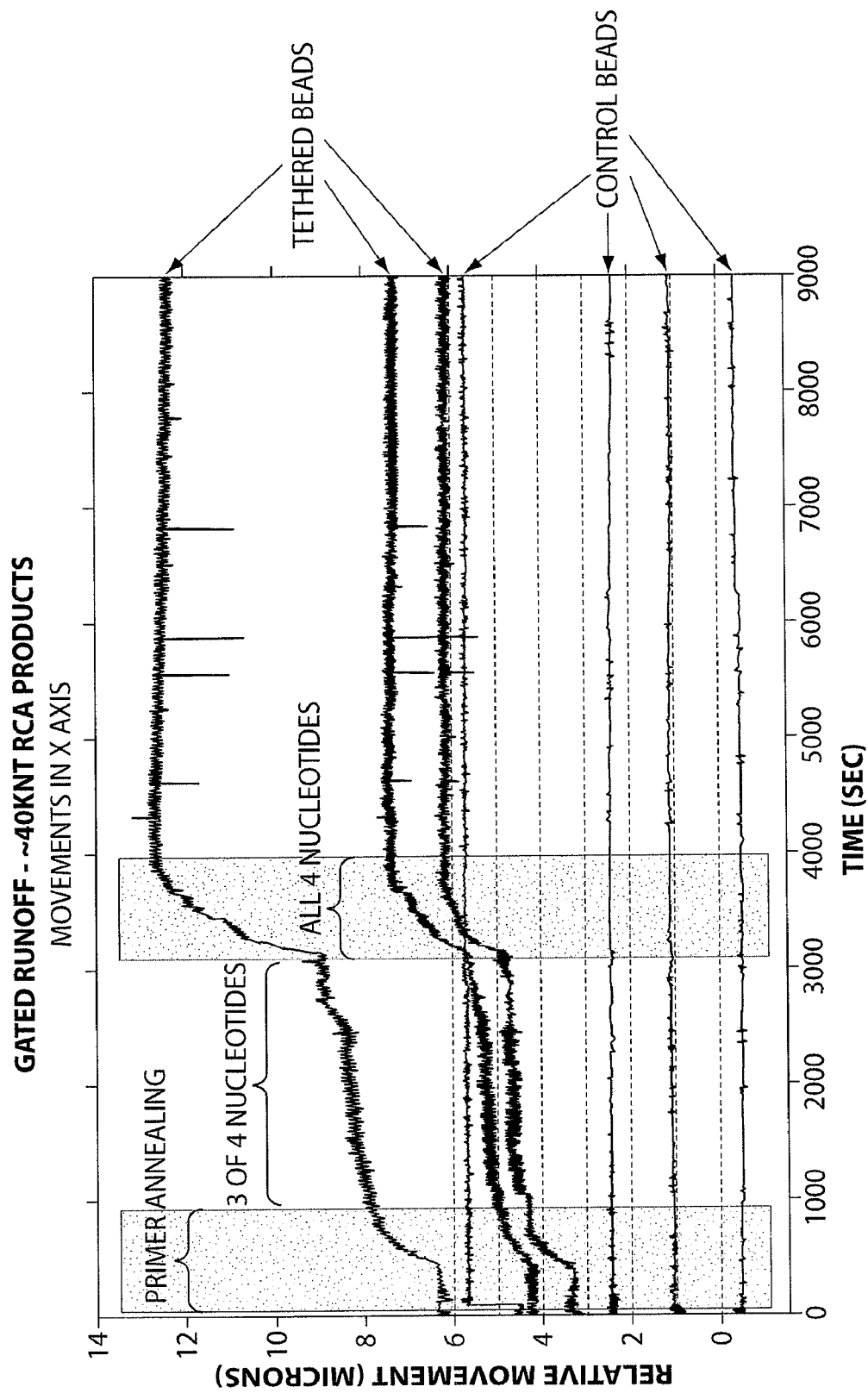
FIG. 22 is a graph showing relative movement data for tethered and control beads.

A second experiment was performed on a slide prepared with the same RCA product and coating. Images were captured continuously for the experiment at a fixed flow rate of 1 pN. In the first 15 minutes, 1 µM of primer was flowed in and the extension due to annealing was captured. Following primer annealing, three of the four non-incorporating nucleotides were flowed in at 200 µM for 30 minutes followed by T4 exo minus DNA polymerase at 100 nM and all four nucleotides. Extension was captured for more than 60 minutes. FIG. 22 shows seven beads that were observed in this experiment. Four of the beads were non-specifically bound to the slide and did not alter position, three beads showed increases in length corresponding to the period when primer was initially flowed in and when each of the four nucleotides was incorporated. In the absence of the required nucleotide, no extension was observed.

Example 2

Error Analysis

The following is a mathematical model relating to the measurements and errors associated with the methods described herein.

Length of Single-Strand DNA.

The persistence length of ssDNA, A, is 0.7 nm (Wuite et al. *Nature* 404, 103-6 (2000)). The approximated worm-like-chain model for ssDNA (Bustamante et al. *Science* 265 1599) (1994)) estimates the end-to-end distance, x, as equation (1) as follows:

$$FA/kT = \frac{1}{4}(1 - x/L)^{-2} - \frac{1}{4} + x/L$$

where k is Boltzmann's constant, T is temperature, and L is the contour length, and A is the persistence length, and F is the force created by the hydrodynamic drag.

Length of Double-Strand DNA.

The persistence length of dsDNA, P, is 53 nm (Bustamante et al. *Science* 265 1599 (1994); Wuite et al. *Nature* 404, 103-6 (2000)). The approximated worm-like chain model for dsDNA (Davenport et al. *Science* 287, 2497-500 (2000)) is given by Eq. (1), but with different values of L and A.

Precision of Length Measurement.

In flow, the precision of bead location is commonly assumed to be 10 nm (Davenport et al. *Science* 287, 2497-500 (2000)). In optical bead experiments, the precision is thought to be 1-7 nm (Davenport et al. *Science* 287, 2497-500 (2000)).

Flow Rate.

The force of extension depends linearly on the flow rate, according to the Stokes-Einstein relation.

Bead Size.

The force of extension depends linearly on the bead size, according to the Stokes-Einstein relation.

Brownian Motion.

The potential felt by the bead is the potential from the stretching of the DNA and the flow force from the fluid (F). The first derivative is the force. The second derivative of the potential, the first derivative of the force, tells us the typical fluctuations:

$$<(dx)^2> = kT/dF/dx \qquad (2)$$

Note that this fluctuation goes to zero as the dsDNA goes to its crystallographic length of 0.34 nm/base. Of course, it takes a very large force to completely straighten out ssDNA (see FIG. 1 of Wuite et al. (*Nature* 404, 103-6 (2000)). However, where ssDNA is longer than dsDNA, dF/dx is easily 10× larger than what it is in the low force situation. Thus, the resolution limit may be improved by an order of magnitude compared to the published 10 nm (Lee et al. *Nature* 439, 621-4 (2006)), by increasing forces to where both ssDNA and dsDNA are almost fully stretched (10-20 pN). It should be noted that equation (2) describes the variance of the instantaneous Brownian motion. The precision of position determination of a bead undergoing Brownian motion is further improved by a factor that scales with the square root of the measurement time. Extrapolating from the published 10 nm at 2 Hz and 2-3 pN (Lee et al. *Nature* 439, 621-4 (2006)), 5 nm should be within reach at 0.5 Hz and 2-3 pN, or below 1 nm at 0.5 Hz and 15-20 pN. Under these parameters, mechanical drifts of the microfluidics platform with respect to the imaging system are likely to be dominant. These drifts cannot be averaged out, but can be corrected for by placing and tracking surface-fixed beads or other fiducial markers. These drift trajectories can be directly subtracted from the length trajectories of tethered, measured beads.

High Versus Low Force.

The length change at high and low force can be of the same order of magnitude. However, the resolution can be 10× better at high force. Thus, it would appear that experiments at high force may be preferable. At or near the low force limit, for an optimally designed experiment, the difference between ssDNA and dsDNA is approximately (see FIG. 1B from Yanagida et al. (*Cold Spring Harb Symp Quant Biol* 47 Pt 1, 177-87 (1983))

$$dL=0.26*N \quad (3)$$

where N=number of bases that differ between ssDNA and dsDNA.

At or near the high force limit, the difference between ssDNA and dsDNA is approximately (see FIG. 1B from Yanagida et al. (*Cold Spring Harb Symp Quant Biol* 47 Pt 1, 177-87 (1983))

$$dL=0.16*N \quad (4)$$

where N=number of bases that differ between ssDNA and dsDNA.

This indicates that the signal will be 40% smaller at high force, but the precision on the measurement will be 10× better. This argues for measurement at high rather than low forces limits. The crossover force is about 10 pN for 48 kb DNA (Yanagida et al. *Cold Spring Harb Symp Quant Biol* 47 Pt 1, 177-87 (1983)) and about 6.5 pN for 10 kb base DNA (Wuite et al. *Nature* 404, 103-6 (2000)).

Wuite et al. (Wuite et al. *Nature* 404, 103-6 (2000)) studied the force dependence of polymerase activity in the case of the T7 DNA polymerase and reported no inhibition on polymerase activity as long as stretching forces were maintained below 12 pN. Such a force is still sufficient to provide a large contrast between single-stranded and double-stranded DNA (see FIG. 1).

Base Extension Estimation—Low Force.

The difference between these two lengths is compared at the resolution, $\epsilon=10$ nm. The probability of an error is p=erfc[dL/(2$\epsilon$)].

| Number of bases different | dL (nm) | p |
|---|---|---|
| 108 | 28 | 0.05 |
| 138 | 36 | 0.01 |
| 185 | 48 | 0.001 |

Base Extension Estimation—High Force.

The difference between these two lengths is to compared at the resolution, $\epsilon=1$ nm. The uncertainty on the dsDNA is very small, since dF/dx is almost infinity, and the uncertainty is coming entirely from the ssDNA. Thus, the probability of an error is p=erfc{dL/[sqrt(2)$\epsilon$]}.

| Number of bases different | dL (nm) | p |
|---|---|---|
| 10 | 1.6 | 0.05 |
| 13 | 2 | 0.01 |
| 16 | 2.7 | 0.001 |

The total length of the DNA does not enter these calculations, except that the crossover between low and high force depends on the DNA length, somewhat less than linearly.

This modeling is based on the approximation that dsDNA inside the ssDNA in the concatamer DNA contributes as it would if it were linear and separate. This should be a reasonable approximation.

At very high forces in fluid flow, the bead may begin to oscillate (potentially due to a fluid flow instability). The force at which this instability occurs is known in the literature.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise to than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for sequencing comprising:
   immobilizing a single stranded nucleic acid target by its 3' end or 5' end to a surface of a substrate, the single-stranded nucleic acid target including a plurality of tandem repeat nucleic acid sequences, the single-stranded nucleic acid target including a detectable moiety at its free end;
   applying at least one oligonucleotide complementary to at least a portion of a tandem repeat single stranded nucleic acid sequence of the nucleic acid target, the at least one oligonucleotide having a known sequence and hybridizing to the at least a portion of the tandem repeat nucleic acid sequence of the single stranded nucleic acid target;
   applying a force to the single stranded nucleic acid target;
   determining with an ion sensitive field effect transistor array and when the force is applied, a change in a length of the single stranded nucleic acid target arising from hybridizing the at least one oligonucleotide, the determining based on a change in a position of the detectable moiety caused by the conversion of single stranded bases to double stranded bases; and
   associating the change in the length of the single stranded nucleic acid target with a nucleotide sequence for the nucleic acid target.

2. The method of claim 1, wherein immobilizing the single stranded nucleic acid target includes coupling the nucleic acid target to a linker or primer secured to the surface of the substrate.

3. The method of claim 1, wherein the force is in a range of approximately 1 pN to approximately 12 pN.

4. The method of claim 1, wherein the force is a flow-based force inducing tension in the nucleic acid target.

5. The method of claim 1, wherein the detectable moiety is responsive to a magnetic force and wherein the force is a magnetic force that induces tension in the nucleic acid target.

6. The method of claim 1, wherein the force is an electrical force that induces tension in the nucleic acid target.

7. The method of claim 1, wherein at least two different forces induce tension in the nucleic acid target.

8. The method of claim 1, wherein the detectable moiety includes a particle or bead.

9. The method of claim 8, wherein the particle or bead is magnetic.

10. The method of claim 1, wherein the detectable moiety includes a magnetic bead, the method further comprising applying a magnetic field proximal to the nucleic acid target.

11. The method of claim 10, wherein the magnetic field provides tension to the nucleic acid target substantially perpendicular to a flow field.

12. The method of claim 11, wherein the tension is substantially parallel to a substrate to which the nucleic acid target is immobilized.

13. The method of claim 10, wherein the magnetic field urges the magnetic bead toward an approximate central locality of a flow field.

14. A method for sequencing comprising:
   immobilizing a single stranded nucleic acid target by its 3' end or 5' end to a surface of a substrate, the single stranded nucleic acid target including a plurality of tandem repeat nucleic acid sequences, the single stranded nucleic acid target including a detectable moiety at its free end;

applying a plurality of oligonucleotides complementary to at least a portion of the tandem repeat nucleic acid sequences, the plurality of oligonucleotides having a known sequencing and hybridizing to the plurality of tandem repeat nucleic acid sequences;

applying a force to the single stranded nucleic acid target;

determining with an ion sensitive field effect transistor array and when the force is applied, a change in a position of the detectable moiety arising from the hybridizing of the plurality of oligonucleotides and determining a change in a length of the single stranded nucleic acid target caused by the conversion of single stranded bases to double stranded bases; and associating the change in the length of the single stranded nucleic acid target with a nucleotide sequence for the single stranded nucleic acid target.

15. The method of claim 14, further comprising applying tension to the single stranded nucleic acid target prior to determining a change in position.

16. The method of claim 15, wherein the detectable moiety includes a magnetic bead and wherein the tension is applied using a magnetic field.

\* \* \* \* \*